US 11,455,597 B2
Sep. 27, 2022

(12) United States Patent
Liberty et al.

(10) Patent No.: US 11,455,597 B2
(45) Date of Patent: Sep. 27, 2022

(54) REMOTELY DIAGNOSING CONDITIONS AND PROVIDING PRESCRIPTIONS USING A MULTI-ACCESS HEALTH CARE PROVIDER PORTAL

(71) Applicant: DAV ACQUISITION CORP., Orlando, FL (US)

(72) Inventors: Michael A. Liberty, Windermere, FL (US); Mike Love, Austin, TX (US)

(73) Assignee: DAV ACQUISITION CORP., Orlando, FL (US)

( * ) Notice: Subject to any disclaimer, the term of this patent is extended or adjusted under 35 U.S.C. 154(b) by 450 days.

(21) Appl. No.: 16/660,609

(22) Filed: Oct. 22, 2019

(65) Prior Publication Data

US 2020/0051691 A1 Feb. 13, 2020

Related U.S. Application Data

(63) Continuation of application No. 14/278,980, filed on May 15, 2014, which is a continuation-in-part of (Continued)

(51) Int. Cl.
*G06Q 10/10* (2012.01)
*G16H 10/60* (2018.01)
(Continued)

(52) U.S. Cl.
CPC ........... *G06Q 10/10* (2013.01); *G06Q 10/107* (2013.01); *G16H 10/60* (2018.01); *G16H 20/10* (2018.01); *G16H 40/67* (2018.01)

(58) Field of Classification Search
CPC ...... G06Q 10/10; G06Q 10/107; G16H 10/60; G16H 20/10; G16H 40/67; G16H 50/20
See application file for complete search history.

(56) References Cited

U.S. PATENT DOCUMENTS

| 5,870,548 A | 2/1999 | Nielsen |
| 6,289,450 B1 | 9/2001 | Pensak et al. |

(Continued)

FOREIGN PATENT DOCUMENTS

| WO | 2008130178 A1 | 10/2008 |
| WO | 2009099928 A2 | 8/2009 |

(Continued)

OTHER PUBLICATIONS

AT&T Healthcare Community Online Portal and Clinical Applications; AB-2256; Retrieved from Internet on Oct. 11, 2011; 3 pages.
(Continued)

*Primary Examiner* — Robert A Sorey
*Assistant Examiner* — Kristine K Rapillo
(74) *Attorney, Agent, or Firm* — Dickinson Wright, PLLC; Stephen A. Mason; Jonathan A. Schnayer

(57) ABSTRACT

Embodiments are directed to providing remote healthcare services including remote diagnostics, and facilitating third-party healthcare payments. In one embodiment, a computer system receives an input including authentication credentials from a healthcare entity, and also requests assistance from another healthcare entity. The computer system authenticates the first healthcare entity using the authentication credentials, receives an input including authentication credentials from the other healthcare entity, and authenticates the other healthcare entity using these authentication credentials. The computer system further receives real-time information related to a health condition of a patient, where the real-time health condition information is provided to the second healthcare entity. The computer system also receives, from the other healthcare entity, diagnostic information related to the patient's health condition, and provides the received diagnostic information to the first healthcare entity, the patient and/or a payment entity.

17 Claims, 19 Drawing Sheets

Related U.S. Application Data application No. 14/263,728, filed on Apr. 28, 2014, now Pat. No. 9,959,385, which is a continuation-in-part of application No. 14/179,999, filed on Feb. 13, 2014, now abandoned.

(60) Provisional application No. 61/765,198, filed on Feb. 15, 2013.

(51) Int. Cl.
    *G16H 40/67*     (2018.01)
    *G16H 20/10*     (2018.01)

(56) References Cited

U.S. PATENT DOCUMENTS

| | | |
|---|---|---|
| 6,701,347 B1 | 3/2004 | Ogilvie |
| 6,907,123 B1 | 6/2005 | Schier |
| 6,978,268 B2 | 12/2005 | Thomas et al. |
| 7,010,616 B2 | 3/2006 | Carlson et al. |
| 7,023,997 B1 | 4/2006 | Schier |
| 7,149,893 B1 | 12/2006 | Leonard et al. |
| 7,558,738 B1 | 7/2009 | Flatt |
| 7,567,660 B2 | 7/2009 | Lemchen et al. |
| 7,949,873 B2 | 5/2011 | Schwartz et al. |
| 7,974,924 B2 | 7/2011 | Holla et al. |
| 8,069,060 B2 | 11/2011 | Tipirneni |
| 8,117,045 B2 | 2/2012 | Lorsch |
| 8,117,646 B2 | 2/2012 | Lorsch |
| 8,121,855 B2 | 2/2012 | Lorsch |
| 8,301,466 B2 | 10/2012 | Lorsch |
| 8,321,240 B2 | 11/2012 | Lorsch |
| 8,332,239 B2 | 12/2012 | Karamchedu et al. |
| 8,352,288 B2 | 1/2013 | Lorsch |
| 8,370,648 B1 | 2/2013 | Natanzon |
| 8,396,803 B1 * | 3/2013 | Dala .............. G16H 80/00 380/231 |
| 8,498,883 B2 | 7/2013 | Lorsch |
| 8,626,532 B2 | 1/2014 | Lorsch |
| 8,645,161 B2 | 2/2014 | Lorsch |
| 2001/0034618 A1 | 10/2001 | Kessler et al. |
| 2001/0039503 A1 | 11/2001 | Chan et al. |
| 2001/0042008 A1 | 11/2001 | Hull et al. |
| 2002/0188467 A1 * | 12/2002 | Eke ................ G16H 20/10 705/2 |
| 2003/0009367 A1 | 1/2003 | Morrison |
| 2004/0034550 A1 | 2/2004 | Menschik et al. |
| 2004/0128163 A1 | 7/2004 | Goodman et al. |
| 2004/0199765 A1 | 10/2004 | Kohane et al. |
| 2005/0149364 A1 | 7/2005 | Ombrellaro |
| 2006/0004588 A1 | 1/2006 | Ananda |
| 2006/0064319 A1 | 3/2006 | Loevner |
| 2006/0277075 A1 | 12/2006 | Salwan |
| 2006/0287890 A1 | 12/2006 | Stead et al. |
| 2007/0198296 A1 | 8/2007 | Pellinat et al. |
| 2007/0233519 A1 | 10/2007 | Lorsch |
| 2008/0004904 A1 | 1/2008 | Tran |
| 2008/0097851 A1 | 4/2008 | Bemmel et al. |
| 2008/0114618 A1 | 5/2008 | Pysnik et al. |
| 2008/0172252 A1 | 7/2008 | Vovan et al. |
| 2009/0055222 A1 | 2/2009 | Lorsch |
| 2009/0055894 A1 | 2/2009 | Lorsch |
| 2009/0100268 A1 | 4/2009 | Garcia et al. |
| 2009/0247836 A1 | 10/2009 | Cole et al. |
| 2010/0131296 A1 | 5/2010 | Knutson |
| 2010/0153135 A1 | 6/2010 | Park |
| 2010/0241595 A1 | 9/2010 | Felsher |
| 2011/0022414 A1 | 1/2011 | Ge et al. |
| 2011/0082711 A1 | 4/2011 | Poeze et al. |
| 2011/0119076 A1 | 5/2011 | Dhoble |
| 2011/0131406 A1 | 6/2011 | Jones et al. |
| 2011/0251855 A1 | 10/2011 | Lorsch |
| 2011/0305335 A1 | 12/2011 | Negishi et al. |
| 2012/0078663 A1 | 3/2012 | Lorsch |
| 2012/0129139 A1 | 5/2012 | Partovi |
| 2012/0166221 A1 | 6/2012 | Phillips |
| 2012/0179908 A1 | 7/2012 | Duma |
| 2012/0330678 A1 | 12/2012 | Kobylevsky et al. |
| 2013/0054273 A1 | 2/2013 | Lorsch |
| 2013/0060576 A1 | 3/2013 | Hamm et al. |
| 2013/0117391 A1 | 5/2013 | Aceves |
| 2013/0138458 A1 | 5/2013 | Lorsch |
| 2013/0159018 A1 | 6/2013 | Lorsch |
| 2013/0173287 A1 * | 7/2013 | Cashman .............. H04N 7/141 705/2 |
| 2013/0179190 A1 * | 7/2013 | Boyer .............. G06Q 20/10 705/3 |
| 2013/0179194 A1 | 7/2013 | Lorsch |
| 2013/0179195 A1 | 7/2013 | Lorsch |
| 2013/0191163 A1 | 7/2013 | Lorsch |
| 2013/0218597 A1 | 8/2013 | Lorsch et al. |
| 2013/0226620 A1 | 8/2013 | Lorsch |
| 2013/0231959 A1 | 9/2013 | Lorsch |
| 2013/0231960 A1 | 9/2013 | Lorsch |
| 2013/0275524 A1 | 10/2013 | Gueramy et al. |
| 2013/0290443 A1 | 10/2013 | Collins et al. |
| 2013/0297341 A1 | 11/2013 | Safranek |
| 2013/0325511 A1 | 12/2013 | Neagle, III |
| 2014/0088998 A1 | 3/2014 | Boyer et al. |
| 2014/0096225 A1 | 4/2014 | Hussain et al. |
| 2014/0134561 A1 | 5/2014 | Smith et al. |
| 2014/0236612 A1 | 8/2014 | Liberty |
| 2014/0236622 A1 | 8/2014 | Southam |
| 2014/0236635 A1 | 8/2014 | Liberty et al. |
| 2017/0235898 A1 | 8/2017 | Coulter et al. |

FOREIGN PATENT DOCUMENTS

| | | |
|---|---|---|
| WO | 2012015543 A2 | 2/2012 |
| WO | 2012148780 A2 | 11/2012 |
| WO | 2013119646 A1 | 8/2013 |
| WO | 2014063162 A1 | 4/2014 |
| WO | 2014127199 A2 | 8/2014 |
| WO | 2015175721 A1 | 11/2015 |

OTHER PUBLICATIONS

Effectual Services; Patentability Search Report—Multi-Access Health Care Provider Portal; dated Jan. 3, 2014; 37 pages.

Tim Churches; BMC Medical Research Methodology, A proposed architecture and method of operation for improving the protection of privacy and confidentiality in disease registers; Published Jan. 6, 2003; 13 pages.

Patent Cooperation Treaty, International Search Report and Written Opinion for PCT/US15/30664; dated Sep. 30, 2015; 13 pages.

Patent Cooperation Treaty, International Search Report and Written Opinion for PCT/US2014/016401; dated May 12, 2014; 8 pages.

Intellectual Property Office of Singapore, Search Report and Written Opinion for Singapore Application No. 11201610509S; dated Nov. 6, 2017; 10 pages.

* cited by examiner

REMOTELY DIAGNOSING CONDITIONS AND PROVIDING PRESCRIPTIONS USING A MULTI-ACCESS HEALTH CARE PROVIDER PORTAL

CROSS-REFERENCE TO RELATED APPLICATIONS

This application is a continuation of U.S. patent application Ser. No. 14/278,980, entitled "Remotely Diagnosing Conditions and Providing Prescriptions Using a Multi-Access Health Care Provider Portal", filed on May 15, 2014, which is a continuation-in-part of U.S. patent application Ser. No. 14/263,728, entitled "Messaging Within a Multi-Access Health Care Provider Portal", filed on Apr. 28, 2014, which is further a continuation-in-part of U.S. patent application Ser. No. 14/179,999, entitled "Multi-Access Health Care Provider Portal", filed on Feb. 13, 2014, which application claims priority to and the benefit of U.S. Provisional Patent Application Ser. No. 61/765,198, filed on Feb. 15, 2013, entitled "Multi-Access Health Care Provider Portal", each of which is incorporated by reference herein in its entirety.

BACKGROUND

Mobile phones and other digital devices have become increasingly popular in recent years. These devices are used on a daily basis for a variety of different tasks. For instance, mobile devices allow users to check email, send and receive instant messages, check calendar items, take notes, set up reminders, browse the internet, play games or perform any number of different actions using specialized applications or "apps". These applications allow mobile devices to communicate with other computer systems and perform a wide variety of network-connected tasks previously not possible with a mobile device.

BRIEF SUMMARY

Embodiments described herein are directed to targeting specific items to health care users based on determined health concerns. In one embodiment, a computer system determines that a user is subscribed to a health care service, where the health care service is configured to facilitate secure communication between the user and other health care entities. The computer system accesses health care information associated with the user. The health care information is stored as part of the health care service. The computer system determines, from the accessed health care information, various health care concerns associated with the user and, based on this determination, provides the user targeted items according to the determined health care concern.

In some embodiments, the health care service is designed to be compliant with communication requirements outlined in the Health Insurance Portability and Accountability Act (HIPAA). In such cases, the user and the various health care entities may be able to communicate with each other in a HIPAA-compliant manner using their own (mobile) computing devices.

Further embodiments are provided for securely messaging a healthcare entity. In one embodiment, a computer system receives an input from a user indicating that a message including text or other characters is to be securely transmitted to a specified healthcare entity. The message is part of a conversation between a user and the specified healthcare entity. The computer system encrypts the characters of the message using at least one encryption algorithm, so that the message is encrypted during the transfer from the user to the specified healthcare entity. The computer system then initiates transmission of the encrypted message such that the encrypted message is sent to the specified healthcare entity. Throughout the process, the encrypted message is transferred in accordance with legal regulations governing healthcare communications.

In another embodiment, a computer system provides a secure messaging service that receives an encrypted message that includes message content intended for a specified healthcare entity. As in the embodiment above, the encrypted message is part of a conversation between a user and the specified healthcare entity. The computer system determines that the encrypted message was received as part of an established session between the secure messaging service and a user-side instance of a messenger application, and transmits the encrypted message to the specified healthcare entity, where the encrypted message is accessible by the specified healthcare entity via an instance of the messenger application.

In other embodiments, methods, systems and computer program products may be provided which provide remote healthcare services including remote diagnostics, and which facilitate third-party healthcare payments. In one embodiment, a computer system receives an input from a first healthcare entity (such as a nurse) where the input includes authentication credentials, and also requests assistance from another healthcare entity (such as a doctor). The computer system authenticates the first healthcare entity using these authentication credentials. The computer system then receives an input from the other healthcare entity, where the input includes authentication credentials identifying the other healthcare entity as one authorized to perform specified healthcare functions. The computer system authenticates the other healthcare entity using these authentication credentials. The computer system further receives real-time information related to a health condition of a patient, where the real-time health condition information is provided to the second healthcare entity. The computer system also receives, from the other healthcare entity, portions of diagnostic information related to the patient's health condition, and provides the received diagnostic information to at least one of the following: the first healthcare entity, the patient and a payment entity.

In another embodiment, a computer system facilitates a third-party healthcare payment by receiving an input from a healthcare entity identifying at least one healthcare item that is to be paid for by a third party, where the healthcare entity is authenticated to a third-party healthcare payment service. The computer system then sends an indication of the identified healthcare item to the third party for payment. The computer system receives authorization from the third party to pay for the identified healthcare item and initiates a transaction conducted by the third-party healthcare payment service, where the transaction allows the third party to pay for the identified healthcare item. The computer system further notifies the third party that the transaction is complete and that the identified healthcare item has been paid for.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be apparent to one of ordinary skill in the art from the description, or may be learned by the practice of the teachings herein. Features and advantages of embodiments described herein may be realized and obtained by means of the instruments and combinations particularly pointed out in the appended claims. Features of the embodiments described herein will become more fully apparent from the following description and appended claims.

BRIEF DESCRIPTION OF THE DRAWINGS

To further clarify the above and other features of the embodiments described herein, a more particular description will be rendered by reference to the appended drawings. It is appreciated that these drawings depict only examples of the embodiments described herein and are therefore not to be considered limiting of its scope. The embodiments will be described and explained with additional specificity and detail through the use of the accompanying drawings in which.

DETAILED DESCRIPTION

Figure 1:
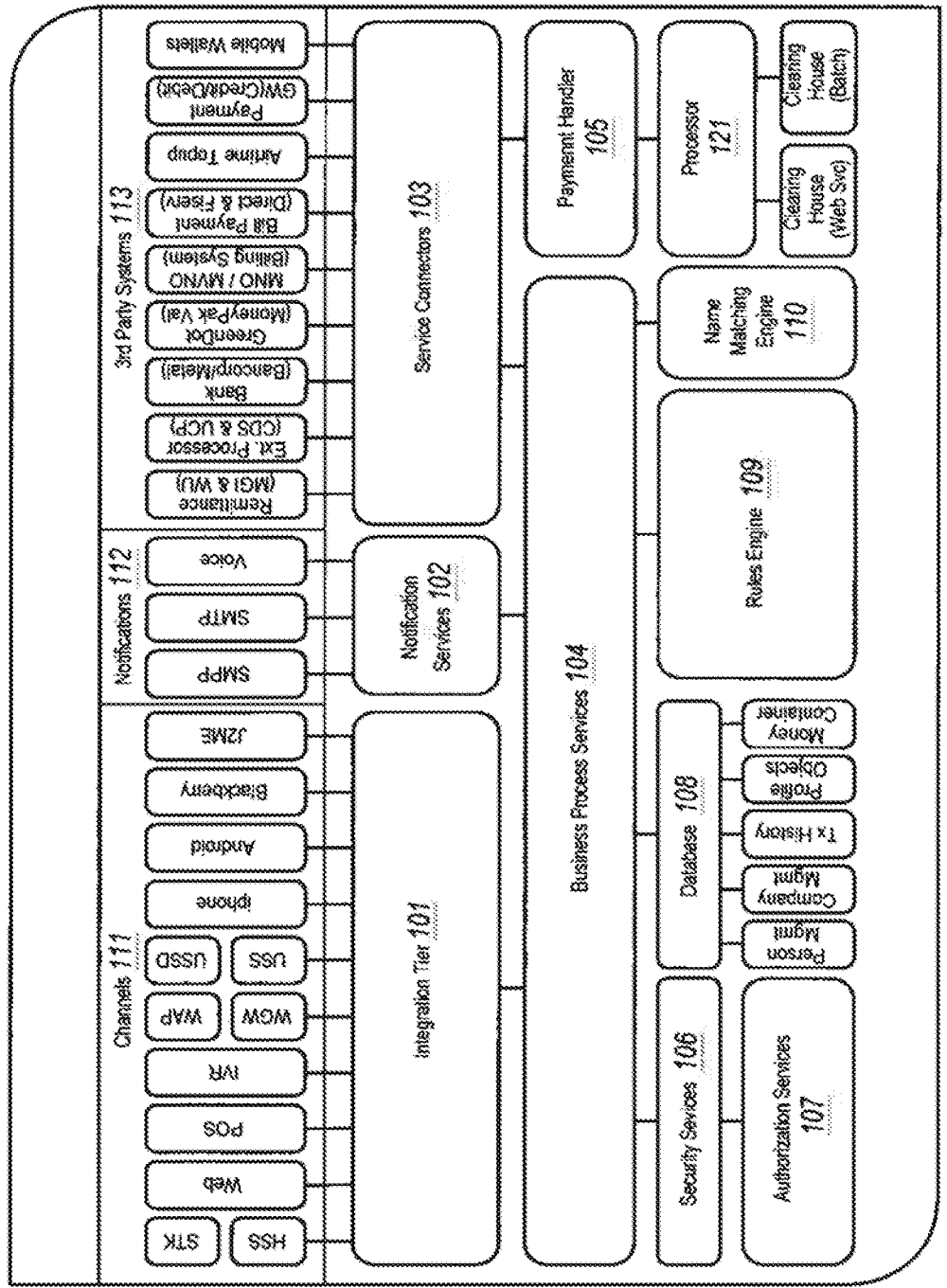
FIG. 1 illustrates a computer architecture in which embodiments described herein may operate including targeting specific items to health care users based on determined health concerns.

Embodiments described herein are directed to targeting specific items to health care users based on determined health concerns. In one embodiment, a computer system determines that a user is subscribed to a health care service, where the health care service is configured to facilitate secure communication between the user and other health care entities. The computer system accesses health care information associated with the user. The health care information is stored as part of the health care service. The computer system determines, from the accessed health care information, various health care concerns associated with the user and, based on this determination, provides the user targeted items according to the determined health care concern.

In some embodiments, the health care service is designed to be compliant with communication requirements outlined in the Health Insurance Portability and Accountability Act (HIPAA). In such cases, the user and the various health care entities may be able to communicate with each other in a HIPAA-compliant manner using their own (mobile) computing devices.

Thus, a multi-access (HIPAA-compliant) health care provider portal may be provided which allows multiple different authenticated providers to access patients' medical records. The portal allows specified portions of the medical records to be transmitted to certain care givers based on a policy defined by the user. The portal further facilitates communication between care givers, including communication of a patient's prescription compliance data.

Further embodiments are provided for securely messaging a healthcare entity. In one embodiment, a computer system receives an input from a user indicating that a message including text or other characters is to be securely transmitted to a specified healthcare entity. The message is part of a conversation between a user and the specified healthcare entity. The computer system encrypts the characters of the message using at least one encryption algorithm, so that the message is encrypted during the transfer from the user to the specified healthcare entity. The computer system then initiates transmission of the encrypted message such that the encrypted message is sent to the specified healthcare entity. Throughout the process, the encrypted message is transferred in accordance with legal regulations governing healthcare communications.

In another embodiment, a computer system provides a secure messaging service that receives an encrypted message that includes message content intended for a specified healthcare entity. As in the embodiment above, the encrypted message is part of a conversation between a user and the specified healthcare entity. The computer system determines that the encrypted message was received as part of an established session between the secure messaging service and a user-side instance of a messenger application, and transmits the encrypted message to the specified healthcare entity, where the encrypted message is accessible by the specified healthcare entity via an instance of the messenger application.

In other embodiments, methods, systems and computer program products may be provided which provide remote healthcare services including remote diagnostics, and which facilitate third-party healthcare payments. In one embodiment, a computer system receives an input from a first healthcare entity (such as a nurse) where the input includes authentication credentials, and also requests assistance from another healthcare entity (such as a doctor). The computer system authenticates the first healthcare entity using these authentication credentials. The computer system then receives an input from the other healthcare entity, where the input includes authentication credentials identifying the other healthcare entity as one authorized to perform specified healthcare functions. The computer system authenticates the other healthcare entity using these authentication credentials. The computer system further receives real-time information related to a health condition of a patient, where the real-time health condition information is provided to the second healthcare entity. The computer system also receives, from the other healthcare entity, portions of diagnostic information related to the patient's health condition, and provides the received diagnostic information to at least one of the following: the first healthcare entity, the patient and a payment entity.

In another embodiment, a computer system facilitates a third-party healthcare payment by receiving an input from a healthcare entity identifying at least one healthcare item that is to be paid for by a third party, where the healthcare entity is authenticated to a third-party healthcare payment service. The computer system then sends an indication of the identified healthcare item to the third party for payment. The computer system receives authorization from the third party to pay for the identified healthcare item and initiates a transaction conducted by the third-party healthcare payment service, where the transaction allows the third party to pay for the identified healthcare item. The computer system further notifies the third party that the transaction is complete and that the identified healthcare item has been paid for.

The following discussion now refers to a number of methods and method acts that may be performed. It should be noted, that although the method acts may be discussed in a certain order or illustrated in a flow chart as occurring in a particular order, no particular ordering is necessarily required unless specifically stated, or required because an act is dependent on another act being completed prior to the act being performed.

Embodiments described herein may comprise or utilize a special purpose or general-purpose computer including computer hardware, such as, for example, one or more processors and system memory, as discussed in greater detail below. Embodiments described herein also include physical and other computer-readable media for carrying or storing computer-executable instructions and/or data structures. Such computer-readable media can be any available media that can be accessed by a general purpose or special purpose computer system. Computer-readable media that store computer-executable instructions in the form of data are computer storage media. Computer-readable media that carry computer-executable instructions are transmission media. Thus, by way of example, and not limitation, embodiments described herein can comprise at least two distinctly different kinds of computer-readable media: computer storage media and transmission media.

Computer storage media includes RAM, ROM, EEPROM, CD-ROM, solid state drives (SSDs) that are based on RAM, Flash memory, phase-change memory (PCM), or other types of memory, or other optical disk storage, magnetic disk storage or other magnetic storage devices, or any other medium which can be used to store desired program code means in the form of computer-executable instructions, data or data structures and which can be accessed by a general purpose or special purpose computer.

A "network" is defined as one or more data links and/or data switches that enable the transport of electronic data between computer systems and/or modules and/or other electronic devices. When information is transferred or provided over a network (either hardwired, wireless, or a combination of hardwired or wireless) to a computer, the computer properly views the connection as a transmission medium. Transmission media can include a network which can be used to carry data or desired program code means in the form of computer-executable instructions or in the form of data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to computer storage media (or vice versa). For example, computer-executable instructions or data structures received over a network or data link can be buffered in RAM within a network interface module (e.g., a network interface card or "NIC"), and then eventually transferred to computer system RAM and/or to less volatile computer storage media at a computer system. Thus, it should be understood that computer storage media can be included in computer system components that also (or even primarily) utilize transmission media.

Computer-executable (or computer-interpretable) instructions comprise, for example, instructions which cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that various embodiments may be practiced in network computing environments with many types of computer system configurations, including personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. Embodiments described herein may also be practiced in distributed system environments where local and remote computer systems that are linked (either by hardwired data links, wireless data links, or by a combination of hardwired and wireless data links) through a network, each perform tasks (e.g. cloud computing, cloud services and the like). In a distributed system environment, program modules may be located in both local and remote memory storage devices.

In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

For instance, cloud computing is currently employed in the marketplace so as to offer ubiquitous and convenient on-demand access to the shared pool of configurable computing resources. Furthermore, the shared pool of configurable computing resources can be rapidly provisioned via virtualization and released with low management effort or service provider interaction, and then scaled accordingly.

A cloud computing model can be composed of various characteristics such as on-demand self-service, broad network access, resource pooling, rapid elasticity, measured service, and so forth. A cloud computing model may also come in the form of various service models such as, for example, Software as a Service ("SaaS"), Platform as a Service ("PaaS"), and Infrastructure as a Service ("IaaS"). The cloud computing model may also be deployed using different deployment models such as private cloud, community cloud, public cloud, hybrid cloud, and so forth. In this description and in the claims, a "cloud computing environment" is an environment in which cloud computing is employed.

Additionally or alternatively, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), and other types of programmable hardware.

Still further, system architectures described herein can include a plurality of independent components that each contribute to the functionality of the system as a whole. This modularity allows for increased flexibility when approaching issues of platform scalability and, to this end, provides a variety of advantages. System complexity and growth can be managed more easily through the use of smaller-scale parts with limited functional scope. Platform fault tolerance is enhanced through the use of these loosely coupled modules. Individual components can be grown incrementally as business needs dictate. Modular development also translates to decreased time to market for new functionality. New functionality can be added or subtracted without impacting the core system.

FIG. 1 illustrates an example system architecture for a mobile wallet platform. Integration tier 101 is configured to manage mobile wallet sessions and maintain integrity of financial transactions. Integration tier 101 can also include a communication (e.g., Web services) API and/or other communication mechanisms to accept messages from channels 111. Other mechanisms include, but are not limited to: International Standards Organization ("ISO") 8583 for Point of Sale ("POS") and Automated Teller Machines ("ATM") devices and Advanced Message Queuing Protocol ("AMQP") for queue based interfaces. Each of channels 111 can be integrated to one or more mechanisms for sending messages to integration tier 101. Notification services 102 is configured to send various notifications through different notification channels 112, such as, for example, Short Message Peer-to-Peer ("SSMP") for Short Messaging Service ("SMS") and Simple Mail Transfer Protocol ("SMTP") for emails. Notification services 102 can be configured through a web services API.

Service connectors 103 are a set of connectors configure to connect to 3rd party systems 113. Each connector can be a separate module intended to integrate an external service to the system architecture. Business process services 104 are configured to implement business workflows, including executing financial transactions, auditing financial transactions, invoking third-party services, handling errors, and logging platform objects. Payment handler 105 is configured to wrap APIs of different payment processors, such as, for example, banking accounts, credit/debit cards or processor 121. Payment handler 105 exposes a common API to facilitate interactions with many different kinds of payment processors.

Security services 106 are configured to perform subscriber authentication. Authorization services 107 are configured to perform client authorization, such as, for example, using a database-based Access Control List ("ACL") table.

Database 108 is configured to manage customer accounts (e.g., storing customer accounts and properties), manage company accounts (e.g., storing company accounts and properties), manage transaction histories (e.g., storing financial transaction details), store customer profiles, storing dictionaries used by the mobile wallet platform, such as, for example, countries, currencies, etc., and managing money containers. Rules engine 109 is configured to gather financial transaction statistics and uses the statistics to provide transaction properties, such as, for example, fees and bonuses. Rules engine 109 is also configured to enforce business constraints, such as, for example, transactions and platform license constraints.

Name matching engine 110 is configured to match different objects according to specified configuration rules. Matching engine 110 can be use to find similarities between names, addresses, etc. Transaction processor 121 is configured to manage financial accounts and transactions. The transaction processor 121 can be used to hold, load, withdraw and deposit funds to mobile wallet accounts. Transaction processor 121 can also be used as a common interface to a third party processor system. When used as a common interface, financial operations may be delegated to the external processor. A Clearing House subsystem of transaction processor 121 can be used to exchange the financial information with a bank.

Components of a mobile wallet platform can be connected to one another over (or be part of) a system bus and/or a network. Networks can include a Local Area Network ("LAN"), a Wide Area Network ("WAN"), and even the Internet. Accordingly, components of the mobile wallet platform can be "in the cloud". As such, mobile wallet platform components as well as any other connected computer systems and their components, can create message related data and exchange message related data (e.g., Internet Protocol ("IP") datagrams and other higher layer protocols that utilize IP datagrams, such as, Transmission Control Protocol ("TCP"), Hypertext Transfer Protocol ("HTTP"), Simple Mail Transfer Protocol ("SMTP"), etc.) over the system bus and/or network.

The components depicted in FIG. 1 can interoperate to provide a number of financial and other services including but not limited to enrolling a customer for a mobile wallet, adding a stored value account (either hosted by a mobile wallet platform or a third party), adding a bank or credit union account to a mobile wallet, adding a debit or credit card account to a mobile wallet, depositing funds in a mobile wallet, withdrawing funds from a mobile wallet, paying bills from a mobile wallet, topping up a prepaid mobile account through a mobile wallet, transferring funds through a mobile wallet (nationally or internationally), making in-store purchases using a mobile wallet, and various other tasks as described herein below. These services will be described in greater detail below with regard to system FIGS. 2-6.

Figure 2:
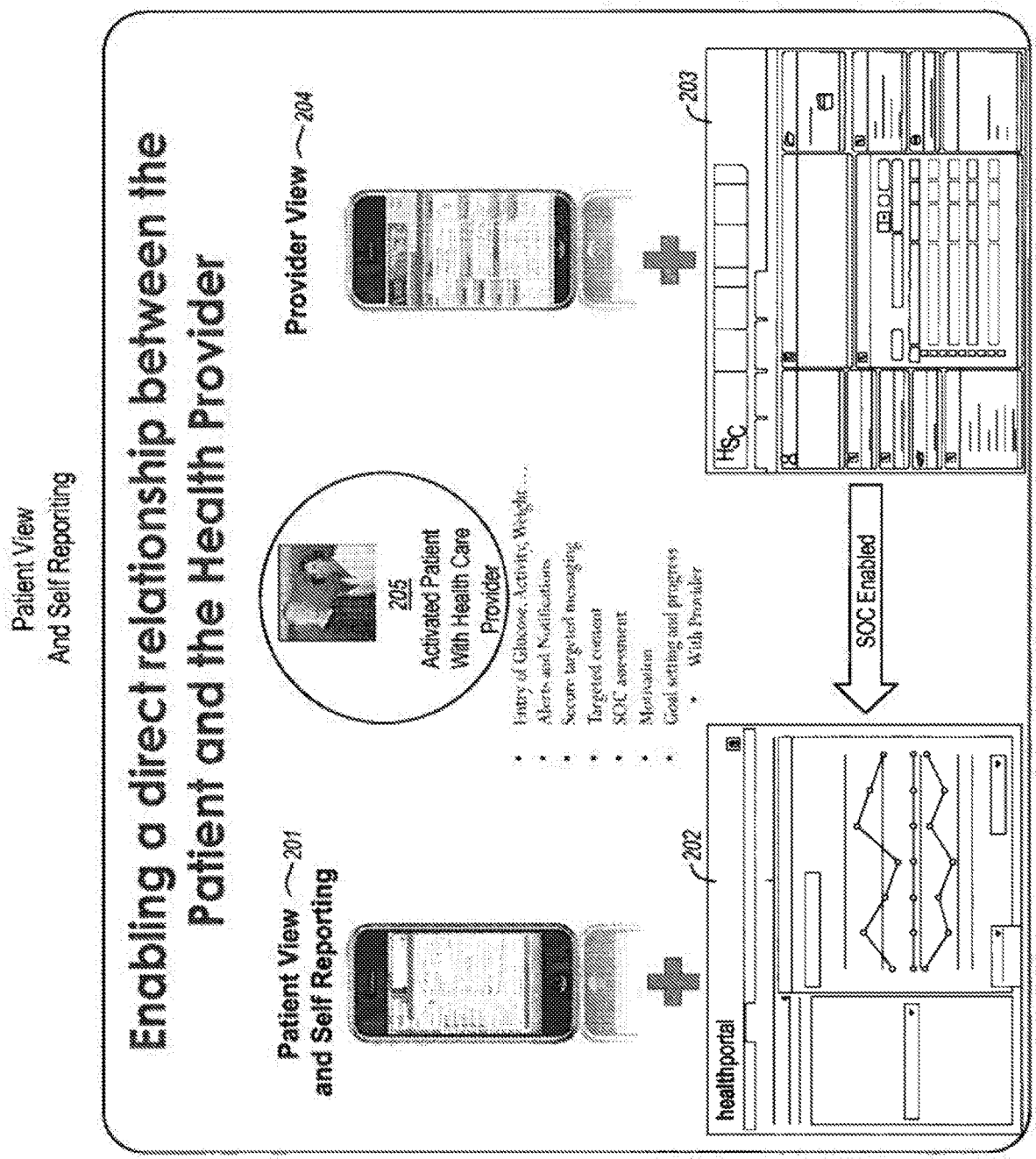
FIG. 2 illustrates an architecture in which patient and provider views of health information are shown.

Embodiments herein are directed to a transparent, seamless, multi-access portal that facilitates communication between parties (e.g. health care entities). As shown in FIG. 2, those parties may include a patient or "user" and the user's health care providers. As used herein, the term "health care provider" may refer to any person or entity that provides health care services to the user. Such people or entities may include, but are not limited to, any of the following: caregivers, doctors, hospitals, emergency medical technicians (EMTs), insurance companies, non-governmental organizations (NGOs), health maintenance organizations (HMOs) and pharmaceutical companies. As will be described further below, the multi-access portal may be accessed by one or more of these health care providers, once the provider is properly authenticated. Upon proper authentication, the health care provider may then be able to access a portion (or all) of the user's medical records or other health-related information. The multi-access portal may implement a service-oriented architecture (SOA) that allows for service-oriented communications (SOCs). These SOCs allow for secure communication between parties and, indeed, allow patients' medical information to be shared in a secure manner.

FIG. 2 illustrates a picture of an activated patient with a health care provider 205. The patient may be asked by their doctor to monitor their condition in some fashion, including monitoring glucose, activity level, weight, medication compliance, or other items. The user may use a mobile device such as a cellular phone, tablet, wearable device or other mobile computing system to report their monitoring/compliance data 201. Alternatively, the user may use a traditional desktop, laptop or other computing device to enter their monitoring data. The data may be entered into a software application such as a health care service. The monitoring data may be stored on the user's device and/or sent to the provider. The user's phone or other mobile device may be used to show their self-reported data. This data may be shown in charts, graphs, text, pictures or a combination thereof. The data may be shown over time, such that the user can view data for the current day, the day before, the week before, the month before, etc. As such, the user can view their self-reported data over time.

The user's compliance over time may be shown, for example, in the plot-line chart of the application 202 in FIG. 2. The health care provider may access the user's monitoring/compliance data upon providing proper authentication credentials. The health care provider's view 204 may be specific to each provider, and may show some or all of the user's compliance data (in application view 203). For example, a doctor may have access to some or all of the user's self-reported data, while a receptionist or data entry clerk may have access to limited portions thereof. Each health care provider's credentials indicate to the system who the provider is and what level of access they have to the user's self-reported data. Using the multi-access portal, the health care provider may contact the user to remind them of goals, to provide motivation or to let them know they may be placing themselves in danger by not taking their medication. The health care provider may also provide tips on how to properly comply with a given prescription or recommendation.

Figure 3:
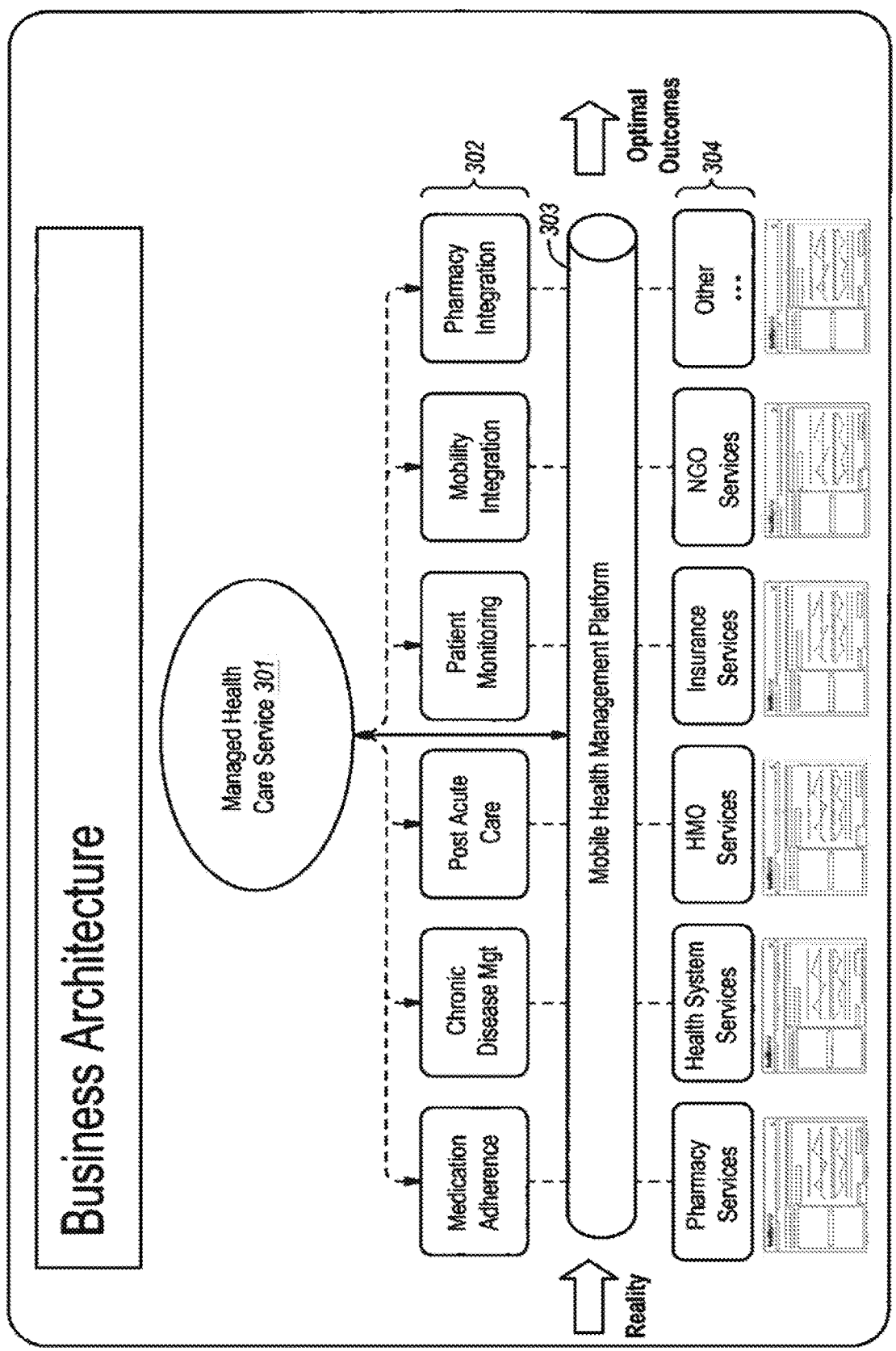
FIG. 3 illustrates a business architecture of a managed health care service.

FIG. 3 illustrates an architecture in which a mobile health management platform 303 is shown. The mobile health management platform may include and may interact with a managed health care (MHC) service 301. The mobile health management platform 303, alone or in combination with MHC service 301, may facilitate communication between users and health care providers. The mobile health management platform 303 may, at least in some embodiments, run on the user's mobile device, and may be used by the user to provide health- or compliance-related information 302. This health- or compliance-related information 302 may include medication adherence information, chronic disease management information, post acute care information, patient monitoring information, mobility integration information and/or pharmacy information. The managed health care service 301 may receive this information 302 from the mobile health management platform 303 and store it, process it and/or pass it on to one or more other health care entities.

Additionally or alternatively, the MHC service 301 may provide the health- or compliance-related information 302 to health care entities (such as doctors) upon authentication of the entity. Still further, the mobile health management platform 303 may allow the health- or compliance-related information to be sent directly to any of the health-care entities 304, without sending it to the MHC service 301 (or in addition to sending it to MHC service 301). Thus, it can be seen, that the MHC service 301 and the mobile health management platform (303) may work in tandem to allow secure communication between parties, and may allow the user to share their medical information with certain specified health care or other authenticated entities.

In some embodiments, a data receiving module may be part of the multi-access health care provider portal. The data receiving module may be configured to receive authentication requests from health care providers. As mentioned above, the health care providers may include caregivers, doctors, hospitals, EMTs, insurance companies, pharmaceutical companies, hospice providers or other persons or entities that provide health care in some manner (including products and services). The authentication requests received from the health care providers may include a perishable, tokenized personal identification number (PIN) assigned to that health care provider. The PIN may be encrypted and tokenized, such that it is only valid for a specified amount of time, or is valid for only a single data transfer. The PIN may be tokenized using a random sequence that is provided along with the PIN upon authentication. Alternatively, the tokenized PIN may be encrypted and tokenized using various other methods.

The health care provider's authentication request may also include an indication of medical records that are to be transferred to the health care provider. If the provider is a doctor, the medical records may be transferred in whole; if the provider is an insurance company or pharmaceutical company, the medical records may be transferred in part. Indeed, the user to whom the medical records belong may decide how much of their data is accessible by the multi-access portal, and how much of their data is transferrable to each health care provider. EMTs, for example, may need to know allergy information, current prescription information and a health history. Other providers may need to know more or less information. The amount of information shared with each health care provider may be outlined in a policy, and may be specified by the patient. Then, the health information may be sent out to the designated health care providers according to the established policy.

Once the authentication request has been received, an authenticating module of the multi-access portal may be configured to authenticate the health care provider using the received tokenized PIN. The authenticating module may use the tokenized, encrypted PIN to verify the identity of the health care provider. Once the provider's identity has been verified, the multi-access portal may retrieve the requested portions of the user's medical records from a data store. The data store may be configured to store medical information for multiple different users in accordance with the security requirements mandated by HIPAA and other prevailing regulatory requirements such as Gramm-Leach/Bliley (GLBA). The data store may be any type of local or distributed store, including a storage area network (SAN). The information stored in the data store may include the user's medical records and a listing of the user's health care providers. This data may then be transmitted or otherwise transferred using a transmitting module of the multi-access portal to the authenticated health care provider.

As mentioned above, the portion of medical information accessible by each health care provider may be variable, and may be specified in a policy associated with the user. The policy (which may be defined by the patient) specifies which health care providers are allowed to access the patient's medical records and which portions of the patient's medical records are accessible by each health care provider.

In some embodiments, the multi-access health care provider portal is compliant with the Health Insurance Portability and Accountability Act (HIPAA). In such cases, the HIPAA-compliant multi-access health care provider portal facilitates transfer of the patient's medical records to properly authenticated health care providers. Once the health care provider has properly authenticated to the HIPAA-compliant portal, the requested portions of the user's medical records are transferred to the provider. In some cases, specific portions of the user's medical records (i.e. those specified in a policy) are automatically transferred to specified health care providers upon the occurrence of one or more specified events.

For example, if a user has not monitored their glucose level within a specified time, that user's doctor, hospice worker, relative or other care giver may be notified by text, email, phone or other means of communication. Portions of that user's medical records (including last known glucose test, current medications, recent illnesses, etc.) may be automatically sent to one or more of the caregivers. It will be understood that this is only one example of an event, and that substantially any number of different events may trigger a communication to a caregiver. That communication may include some portion of the user's medical records, and may include information that is specifically pertinent to that caregiver. In some cases, instead of automatically transferring portions of the user's medical records to the caregivers upon the occurrence of an event, the caregivers are merely notified that an event has occurred, and that they are to log in to the multi-access portal to receive more information.

Still further, the HIPAA-compliant multi-access health care provider portal may be accountable care organization (ACO)-compliant. ACOs typically provide services to hospitals, and are paid when they are in compliance with a set of accountability rules. As such, upon determining that an ACO has complied with the regulations, the ACO may be paid (by any of the health care providers) through the multi-access health care provider portal.

As illustrated in FIG. 3, a HIPAA-compliant portal may include a medication adherence module, which may be configured to monitor the user's medication usage. The medication adherence module may receive medication usage inputs from the user, and further communicate the user's medication usage to one or more of the health care providers (as specified by a policy). The user may be incented to provide their medication usage information in a variety of ways. For instance, the user may receive a reward in their mobile wallet for providing their medication usage. This mobile wallet reward may be provided by an insurance or pharmaceutical company. The reward may be coupon, buy-one-get-one-free offer, a monetary reward, a discount on a specific product, or other type of reward. Accordingly, in one example, a user may enter their compliance data, a pharmaceutical company may access that portion of the user's medical records using their tokenized PIN, and provide the user with rewards based on their compliance. In this manner, the multi-access portal may be used to monitor aspects of a user's chronic disease, or home hospice care, or any of a variety of different medical conditions or procedures.

Further describing FIG. 3, a HIPAA-compliant portal may include a breach notification module (as one of the "Other" nodes referenced in health care entities 304). The breach notification module is operable to track and report unauthorized disclosure of medical records as required under the Health Information Technology for Economic and Clinical Health (HITECH) Act portion of the American Recovery and Reinvestment Act (ARRA). In accordance with the requirements mandated under HITECH, this module would provide the necessary information and process to allow the reporting organization to notify all individuals whose data was breached within the required timeframe.

Figure 4:
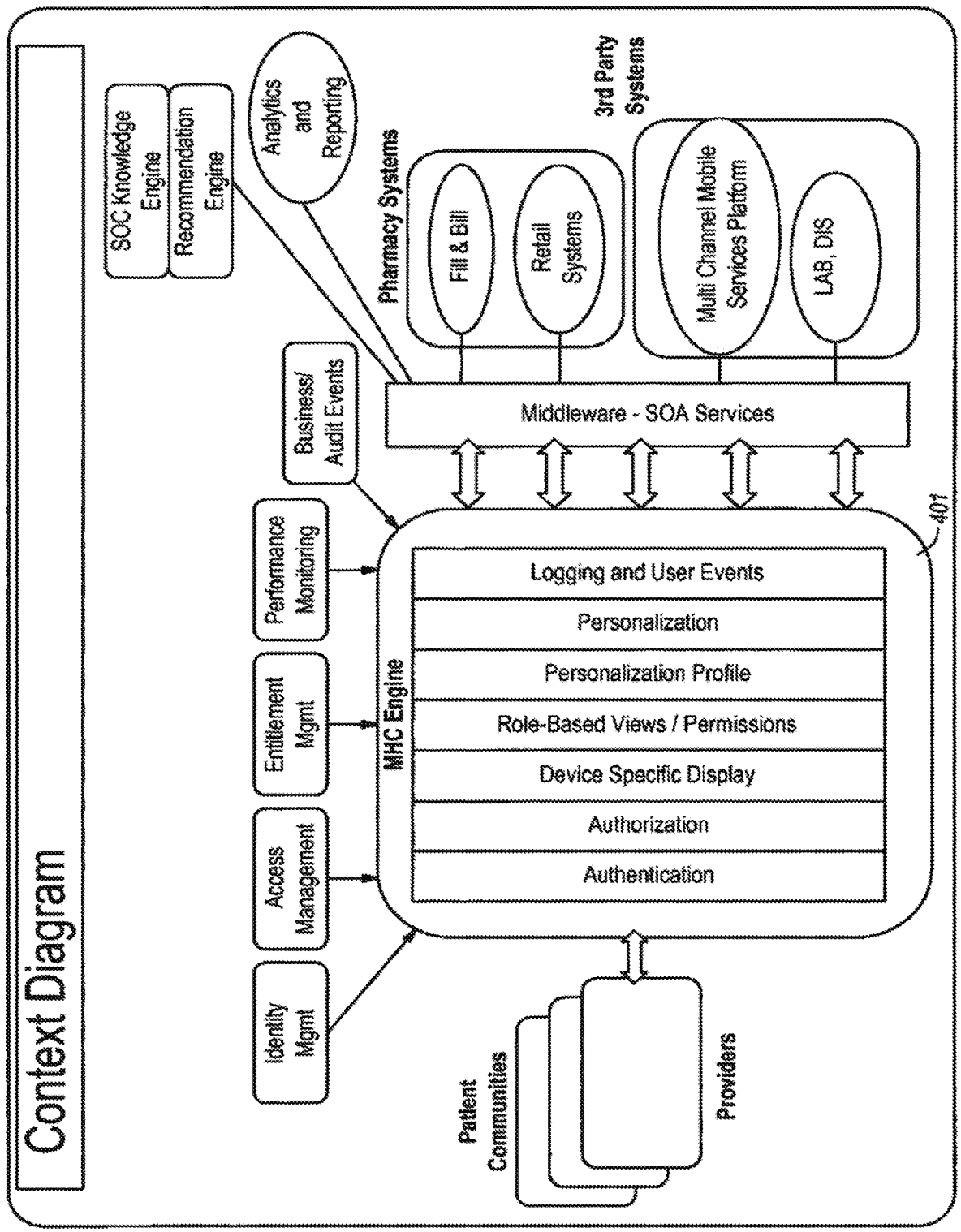
FIG. 4 illustrates a context diagram that includes providers, service-oriented architectures and purpose-based engines.

FIG. 4 describes an architecture which shows various components of a health care engine 401. The health care engine 401 may include the multi-access portal as a component part, or may itself comprise the multi-access portal. The health care engine 401 may include modules for authentication, authorization, device-specific display, role-based (e.g. policy-based) access to the user's data, personalization and personalization profiling, logging and user events. The health care engine 401 may thus facilitate the authentication of users (e.g. patients) and health care providers. Once authenticated, the MHC engine 401 can determine what the user is allowed to access. As mentioned above, different health care providers may have different roles regarding the user's health, and may thus need access to different portions of the user's health information. The health information may be distributed to providers based on predefined policies, and may be personalized for each provider. Thus, doctors may have one view of the user's data, EMTs may have a different view, pharmacists may have another view and hospice caregivers may have still a different view. The MHC engine 401 can ensure that each health care provider receives personalized data, in the format that they prefer.

The health care engine may further interact with other internal or external services. These services may allow interaction with pharmacy systems (including billing and retail systems), 3.sup.rd party systems (including mobile wallet systems), analytics and reporting systems and other systems (as shown in greater detail with regard to the enterprise portal platform 601 in FIG. 6). The MHC engine 401 may be configured to provide certain portions of the user's health information to analytics and reporting services that aggregate information for a wide variety of users. This information may be anonymized so that it is not traceable back to individual users. The user's (anonymized) information may also be sent to recommendation services or engines that take a set of facts (e.g. a medical history along with prescription information) and provide diagnostic recommendations to a health care provider. Still further, other services provided by a service-oriented architecture may be used. These services may allow users to pay bills (e.g. using a mobile wallet application), purchase products, check lab results from outside labs, or perform other functions.

Figure 6:
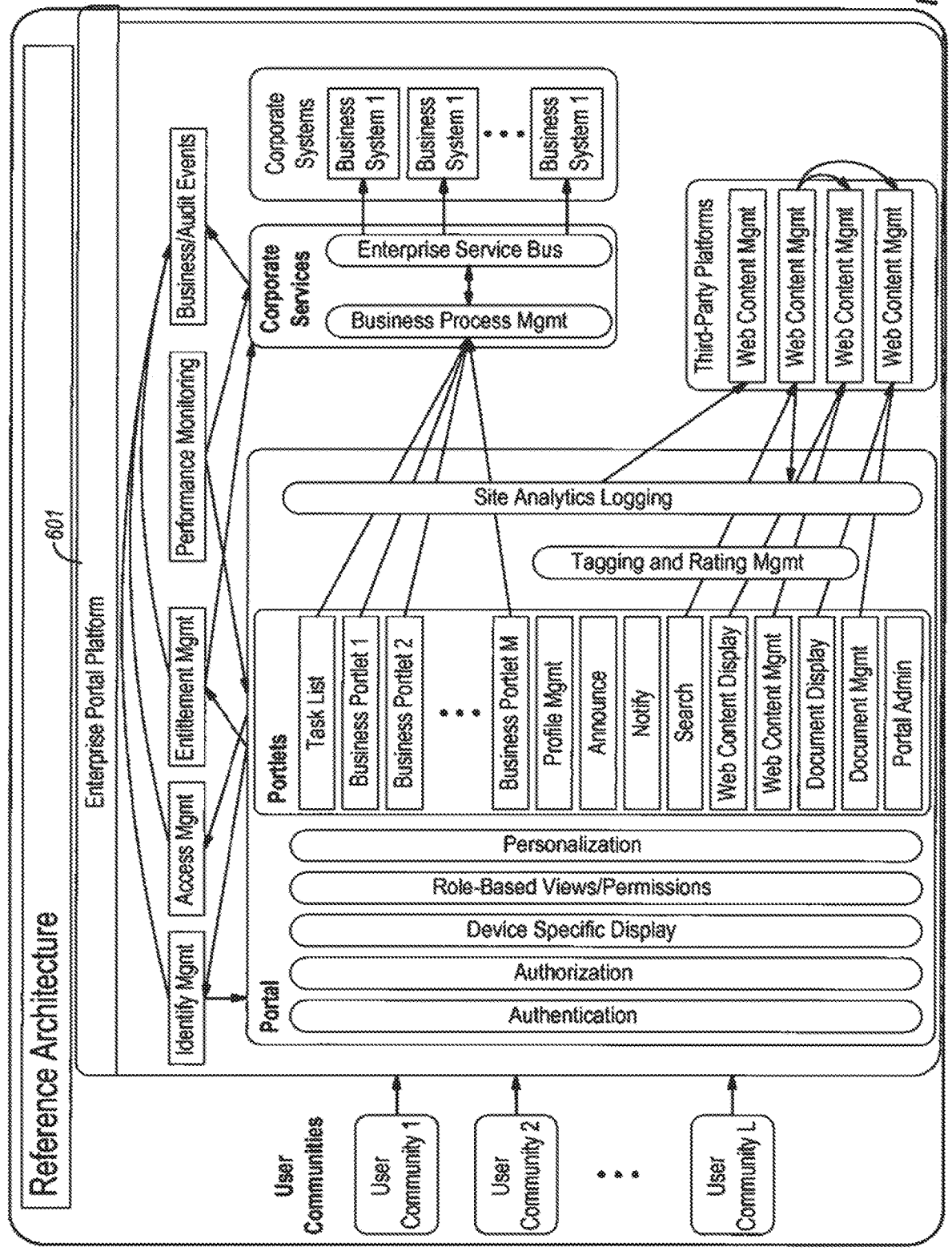
FIG. 6 illustrates a reference architecture for one embodiment of an enterprise portal platform.

Indeed, as shown in the enterprise portal platform of FIG. 6, other third-party platforms may be integrated such as web analytics, enterprise search, web content management and document management. It should be noted that these are merely examples, and that many other third party services or other services may be used. For instance, the enterprise portal platform 601 of FIG. 6 implements corporate services that provide business process management, enterprise service business systems. These services may, in turn, interact with other portal services, as generally described with reference to FIG. 4.

Figure 5:
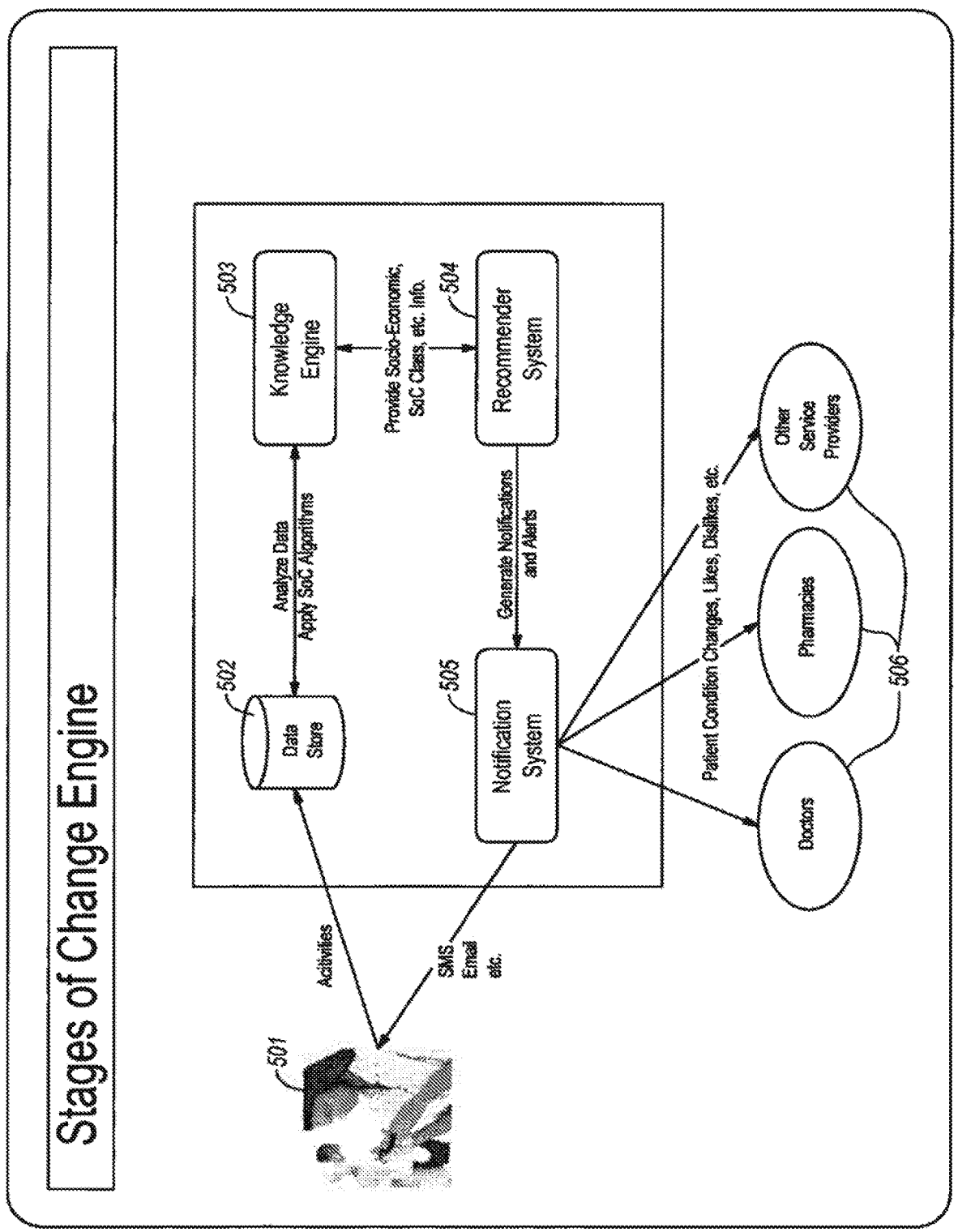
FIG. 5 illustrates various stages of change within a set of purpose-based engines.

In some embodiments, as shown in FIG. 5, the health engine 401 of FIG. 4 may be used to provide recommendations to care givers. For instance, a knowledge engine 503 may look at the user's medical records and determine that the user 501 regularly takes their heart medication two times per day. The user's medical records may be stored in data store 502, and may be accessible to authorized users. If the user hasn't taken their medication, and hasn't responded for a certain period of time, the user's medical records may be transferred to certain care givers including relatives or hospice care givers 506. If the care givers, after reviewing the medical records, indicate that there may be a problem, an EMT may be dispatched to the user 501.

The recommender system 504 may generate a recommendation that is specific to user 501. The recommender system 504 may send the recommendation to the notification engine 505 which distributes the recommendation to the appropriate health care entities 506. For instance, the EMT in the example above may be provided with a recommendation specifically for that patient, based on their medical history, current medications, recent (or long-term) compliance data, etc. The notifications engine 505 may send notices (including the generated recommendations) to the proper care givers, including doctors, pharmacies, hospitals and other care givers 506. The notification engine may, accordingly, notify a heart doctor that the patient has not taken their heart medication, and that an EMT/ambulance will be bringing them to the hospital shortly. The heart doctor may then be ready to help the patient, already having a recommendation of what the potential problems could be based on the user's medical records and prescription compliance history.

Figure 7:
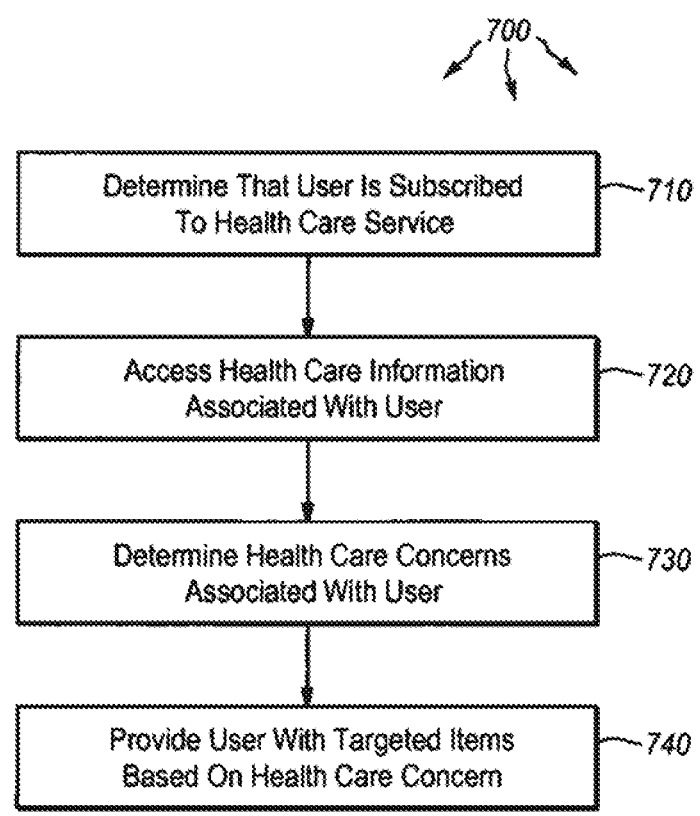
FIG. 7 illustrates a flowchart of an example method for targeting specific items to health care users based on determined health concerns.
Figure 8:
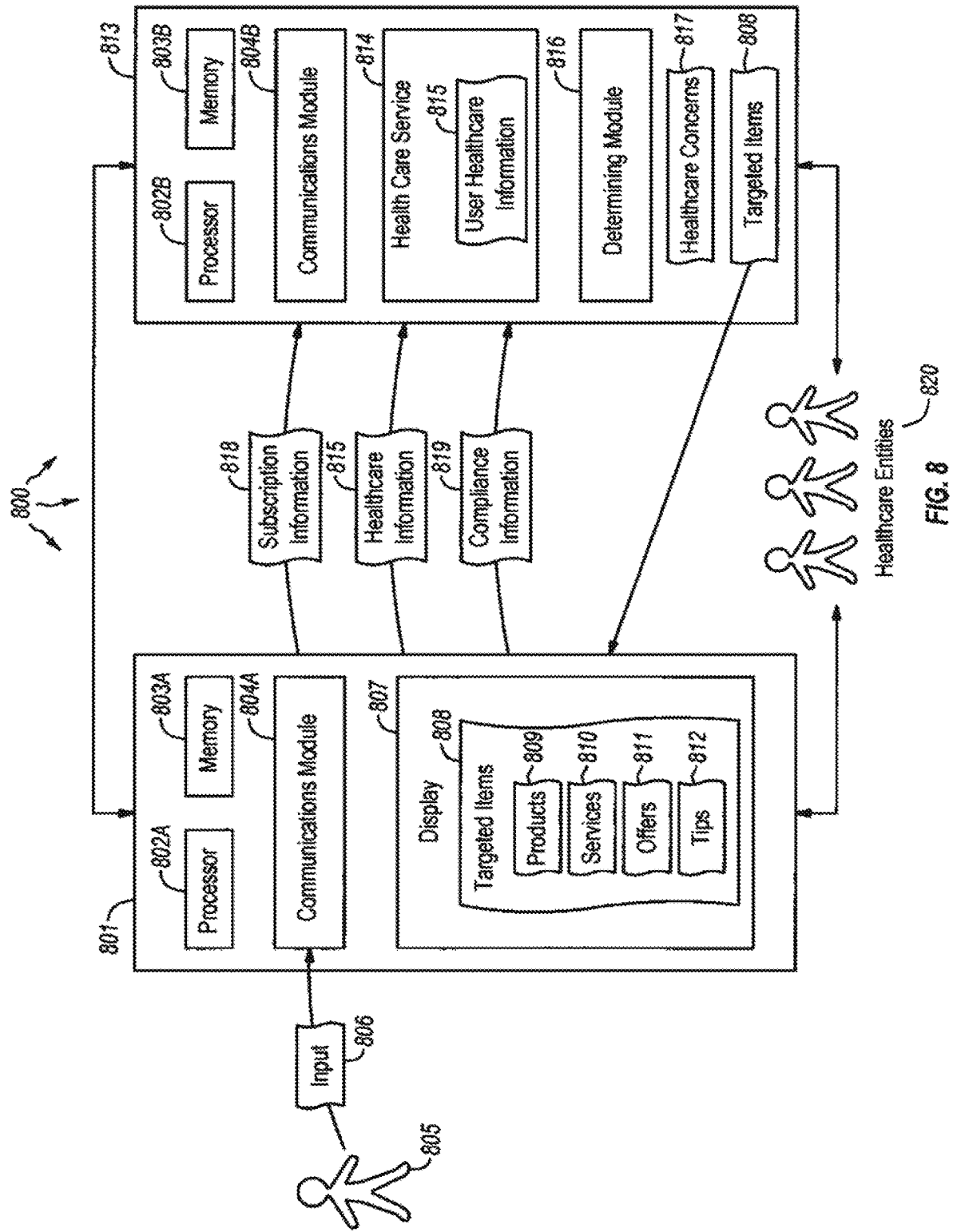
FIG. 8 illustrates a computer architecture in which embodiments may operate including targeting specific items to health care users based on determined health concerns.

Turning now to FIG. 7, a flowchart is illustrated of a method 700 for targeting specific items to health care users based on determined health concerns. The method 700 will now be described with frequent reference to the components and data of environment 800 of FIG. 8.

Method 700 includes determining that a user is subscribed to a health care service, where the health care service is configured to facilitate secure communication between the user and one or more other health care entities (710). For example, user 805 may provide input 806 to computer system 801 indicating that the user intends to subscribe to health care service 814. The user's subscription information 818 may be transferred from computer system 801 to computer system 813. In some embodiments, computer system 801 is a mobile computer system while computer system 813 is a server computer system. Each computer system includes a hardware processor 802A/802B, memory 803A/803B and a communications module 804A/804B, respectively. The communications modules may be used to communicate with other computer systems over wired or wireless communication means (such as Ethernet network cards, WiFi radios, GPS radios, Bluetooth radios or similar). The health care service 814 may be hosted by computer system 813, which itself may be a local or distributed (e.g. cloud) computing system. The health care service 814 may receive the user's subscription information 818 and subscribe the user to the service. In this process, the user becomes a member of the health care service 814.

In some embodiments, the health care service 814 is the same as (or is substantially the same as) the multi-access portal described above. In this regard, the health care service 814 can facilitate secure (and, at least in some cases, HIPAA-compliant) communication between user 805 and various health care entities 820. While shown as running within computer system 813, the health care service 814 may also be run on computer system 801 (in addition to or as an alternative to running on computer system 813). In some cases, the health care service 814 may have a client aspect and a server aspect. Indeed, the computer system 801 may be a mobile computer system that runs a client-side application portion of the health care service 814. As mentioned previously, the health care service 814 may comprise the multi-access portal application mentioned above. The multi-access portal application may be displayed in display 807 of computer system 801.

Method 700 next includes accessing one or more portions of health care information associated with the user, where the health care information is stored as part of the health care service (720). The user 805 may submit subscription information 818 that includes health care information. This information may be submitted upon signing up for the health care service 814. The health care information may include all or parts of a user's medical records including past or present conditions, past or present medications, past or present caregivers, and other health-related information. This user health care information 815 may be submitted as part of the subscribing process, or may be submitted at some other time. In some cases, such as with prescription compliance information, the information 815 may be sent on a continual basis (e.g. daily or weekly). The information may then be stored as part of the health care service 814, or may be stored elsewhere. The computer system 813 may then access the user health care information 815 as needed in order to perform functions approved by the user 805.

Method 700 further includes determining, from the accessed health care information, one or more health care concerns associated with the user (730). The determining module 816 may determine, for example, based on the health care information 815 that user 805 has one or more health concerns (e.g. the user is diabetic, or is supposed to be taking a blood thinner, or any of thousands of other health concerns). These health concerns may be simple or complex, and may be life-threatening or benign. Regardless, the determining module 816 may determine various health concerns associated with the user 805. These health concerns may be based on previous illnesses, surgeries, allergies, diseases, complications, emergency procedures, rehabilitation information, prescriptions, dietary restrictions or other information.

Upon determining health care concerns 817 associated with the user, the determining module may then provide the user one or more targeted items based on the determined health care concern (740). The targeted items may comprise goods or services, for example, The targeted items 808 may be products 809, services 810, offers 811, tips 812 or other items such as coupons or discounts that the user may need as a result of their determined health care concerns 817 or conditions. Accordingly, a drug manufacturer may be able to provide prescription discounts directly to a user that has been prescribed a drug that they produce. Similarly, a wheelchair manufacturer may be able to provide discounts or services (such as house pickup or a house sales call) to show their wheelchair products. Healthy food manufacturers may be able to provide food supplement samples or free products or buy-one-get-one-free offers, or tips on how to make healthy snacks to patients or other users that have been given dietary restrictions.

As one will see, many different products, services or other items may be provided to users who are likely to use those items, and might really need those items (e.g. a wheelchair). It will be understood that, at least in some embodiments, manufacturers, advertisers or others wanting to provide targeted items 808 may be limited by the user's choices. For example, the user 805 may opt in to receive certain offers, products, services or tips, or may opt out of others, or may opt out of all, or may opt in to all. As such, the user will not be bombarded by unwanted offers. On the flipside, the user may receive valuable and needed goods or services at a substantial discount by opting in to such a service.

In some cases, the targeted goods or services, etc. (i.e. 809-812) may be presented within the health care service (i.e. the multi-access portal application) 814. The targeted items 808 may be displayed on display 807 for viewing by the user 805. The user may browse through the various tips, offers, services and/or products offered by different manufactures, service providers, health care entities 820 or other providers. In some cases, a health care entity such as a doctor or pharmacist may provide targeted tips to the user based on at least one determined health care concern associated with that user. The tip may be a reminder to take a pill, or a reminder of a goal to lose weight, or a link to an exercise routine or video, or may be a motivational quote, or any other information usable by the user. The tip may, for example, educate the user about new information related to their health care concern 817. Or, the tip may a reminder to refill a prescription, and may explain the benefits of taking the prescribed medication.

Prescription information may be provided by the user 805 and may be stored as part of health care information 815. The determining module 816 may determine which goods or services might be associated with of useful for users of a certain medication or combination of medications. The determined targeted items 808 may then be sent to the user based on their prescription information. The targeted items may include offers 811 for cheaper refills, offers to refill at different local pharmacies, offers to get other medications at cheaper prices upon fulfillment of a given prescription, etc. Over time, the user's compliance with the prescription may be monitored.

For instance, the user may submit prescription compliance information 819 on a daily, weekly or other basis. Then, based on the user's compliance, the user may receive more or fewer rewards. If the user is fully compliant with a prescription, the user may receive a greater discount for the next prescription fulfillment. If the user complies for a given length of time, he or she may receive a reward upon successful completion of that time period. The reward may be based on the prescription taken, or may be based on health concerns associated with that prescription. For example, cholesterol reducing drugs are often associated with heart disease. If heart disease is a determined health concern for a given patient, the targeted items 808 may each be related to alleviating symptoms of or causes of heart disease. The reward may be provided to the user's mobile device via an application such as a mobile wallet application. The mobile wallet application may allow the user to immediately use the reward to purchase a product or service or redeem an offer. The manufacturer, service provider or other provider of targeted items 808 may then be notified that the user purchased the targeted goods or services, or redeemed the offer or viewed the tip. As such, the targeted items provider may be apprised as to the effectiveness of their offer, tip, good or service.

Still further, it should be noted that the user 805 and/or the health care entities 820 may be asked to authenticate to the health care service 814 before being granted access to or being able to alter the user's health care information 815. In some embodiments, the user 805 and the health care entities may be assigned unique identifiers. These unique identifiers may be tokenized, personal identification numbers (PINs). By verifying the unique identifiers, the health care service 814 may be able to ensure that only authorized users access the user's health care information 815. Once authenticated, users may use the health care service 814 to communicate with each other in real-time and, at least in some cases, using their own mobile devices or other computer systems. These communications may occur in a HIPAA-compliant manner, which preserves the user's privacy.

In some cases, all or a portion of the user's health care information 815 may be automatically transferred to one or more of the health care entities 820 upon the occurrence of a specified event. For instance, if a diabetic user has an abnormally low reading, certain caregivers, relatives, doctors or other entities may be notified via email, text message, voice message or other means. Many other scenarios are possible. The notifications may be sent to a preset list of people, depending on the event that occurred, and may send a predetermined amount of health care information 815 also based on which event occurred. In cases where a doctor is notified of an event, the doctor may perform a remote diagnostic based on the information available to them (i.e. the information provided in the event notification). The doctor may then provide this remote diagnostic to one or more other health care entities 820. In this manner, doctors and other caregivers may share pertinent information about a patient, which may help to save a patient's life.

Figure 9:
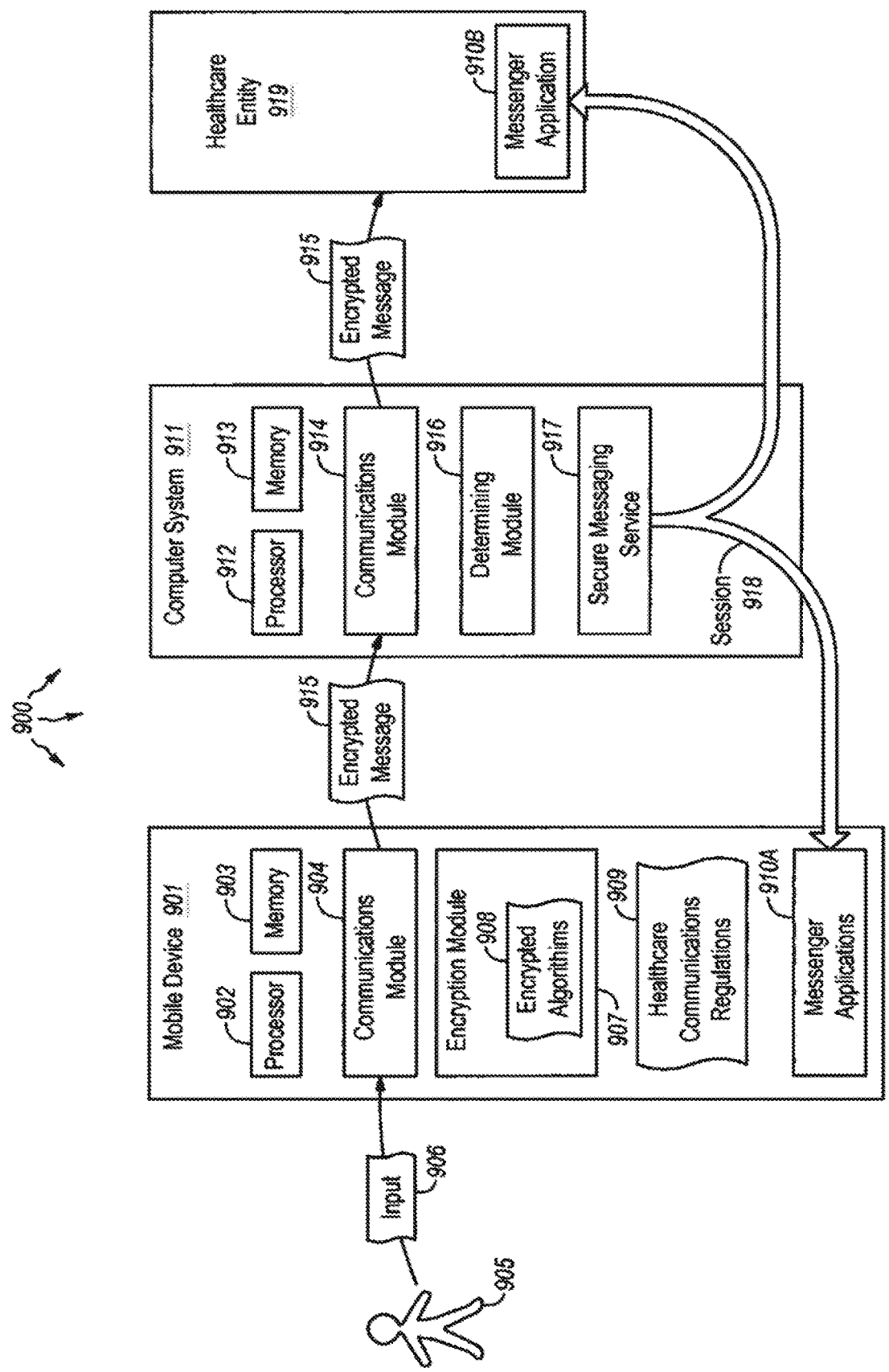
FIG. 9 illustrates a computer architecture in which embodiments may operate including securely messaging a healthcare entity.

Turning now to FIG. 9, a computer architecture 900 is illustrated in which at least one embodiment may be employed. Computer architecture 900 includes multiple computer systems including mobile device 901, computer system 911 and any computer systems run by the various healthcare entities 919. As shown in FIG. 9, mobile device 901 and computer system 911 each include a processor 902/912 and memory 903/913. Each computing system also includes a communications module 904/914 that allows the computer system to communicate with other computer systems via wired or wireless communication means. In most cases, mobile device 901 will be a single, mobile computing device such as a mobile phone (smart phone or feature phone), laptop, tablet, wearable computing device or other mobile device. This mobile device 901, however, may include multiple processors or types of memory, and may draw on shared (e.g. cloud) computing resources when necessary or desired. Computer system 911 may be any type of local or distributed computer system, including a cloud computing system. The computer system 911 may also be mobile in some embodiments, and may similarly have any number of physical processors, memory types or other hardware. Each of the computing systems includes modules for performing a variety of different functions.

For example, mobile device 901 includes encryption module 907. The encryption module 907 includes various encryption algorithms 908 for encrypting messages. In some cases, user 905 may desire to have the messages they send encrypted. For example, if user 905 is using messenger application 910A to communicate with another user, the user 905 may indicate via a selectable option in the messenger application 910A that messages are to be encrypted. The user may choose whether to encrypt a single message or set of messages, all messages in a given conversation, or all messages all the time. Additionally or alternatively, messages may be encrypted according to a policy established by the user 905 or by another user such as an administrator. The policy may indicate that messages between certain specified entities or persons are to be encrypted, or messages between certain types of entities or persons are to be encrypted or messages sent at a certain time of day or from certain locations (e.g. from a hospital, pharmacy or other healthcare entity's location). The encryption module 907 may use any one or more encryption algorithms 908 to encrypt outgoing messages and decrypt incoming messages. In some embodiments, the encryption module 907 may be part of the messenger application 910A. In other cases, it may be a standalone module.

As will be discussed further below with regard to methods 1000 and 1100 of FIGS. 10 and 11, the messenger application 910A may be used to send encrypted messages (e.g. 915) from users (e.g. patients) to healthcare entities (e.g. 919) including doctors, emergency medical technicians (EMTs), pharmacists, hospice providers, nurses, doctor's offices, hospitals, pharmacies and other healthcare entities. The messenger application (e.g. 910B) may also be used by these entities to send messages amongst themselves. For example, a user may send an encrypted message 915 to a doctor indicating that a previously prescribed medication needs a refill, or that a new prescription is needed. After confirming the need for this medication, the doctor may use his or her messenger application 910B to send an encrypted message to a selected pharmacy or pharmacist (e.g. one that is currently near the user that requested the medication). Upon filling the prescription, the pharmacy or pharmacist may then use the messenger application 910B to notify the user 905 that their prescription has been filled and is ready for pickup. As will be appreciated, this is only one among many different examples of entities securely messaging each other using a secure messaging service 917. Additional examples will be provided below, although it will be understood that these are merely a small number of examples among a plurality of possible use cases.

The computer system 911 also includes modules for facilitating secure messaging between parties, especially between patients and healthcare entities. Indeed, at least in some embodiments, the secure messaging service 917 may be configured to facilitate secure communication that complies with applicable regulations governing health- and healthcare-related communications. The secure messaging service 917 may be any type of function, application or service that allows users to authenticate, create a session, and transfer messages securely. For example, user 905 may provide input 906 logging in (or authenticating) via their messenger application 910A. The user may authenticate to the messenger application 910A directly, or may use the messenger application as a conduit to authenticate to the secure messaging service 917. Indeed, in some cases, logging in to the messenger application 910A may automatically authenticate the user 905 to the secure messaging service 917. Once the user 905 (or healthcare entity 919) is authenticated to the secure messaging service 917, the secure messaging service establishes a session 918 between the user (or healthcare entity) and the service.

The session established between the user or entity and the secure messaging service 917 allows the user or entity to send secure, encrypted messages to other parties that are similarly authenticated. The secure messaging service 917 may operate in the cloud, and may thus allow any user with an internet connection to send messages using the messenger. The secure messaging service 917 thus avoids the traditional (and unsecure) short message service (SMS), allowing user to send text messages (or messages including pictures, videos, or other files) using messenger applications. At least in some embodiments, these messenger applications are configured to send push messages to each other. The user's text and other data may be transferred in these push messages. The push messages may be encrypted and otherwise processed by the secure messaging service 917. Other processing may include ensuring that the messages are backed up and stored so that they are retrievable and auditable per healthcare communications regulations 909 (e.g. HIPAA). Alternatively, if the message is a privileged communication between the user and a lawyer, for example, the messages may not be stored and, conversely, may perish automatically upon being delivered, or upon termination of the conversation. Various regulations may prompt changes or updates in the secure messaging service 917. These can easily be added and promulgated in real time. These and other concepts will be explained further below with regard to methods 1000 and 1100 of FIGS. 10 and 11, respectively.

Figure 10:
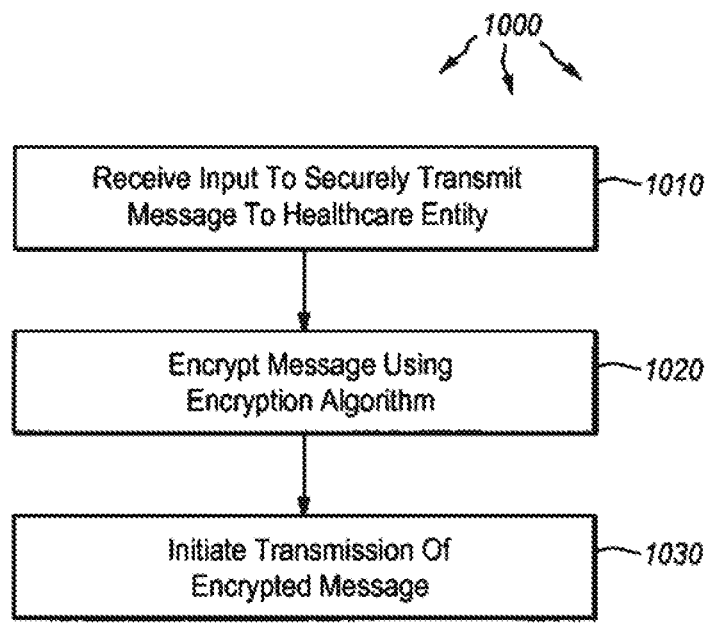
FIG. 10 illustrates a flowchart of an example method for securely messaging a healthcare entity.
Figure 11:
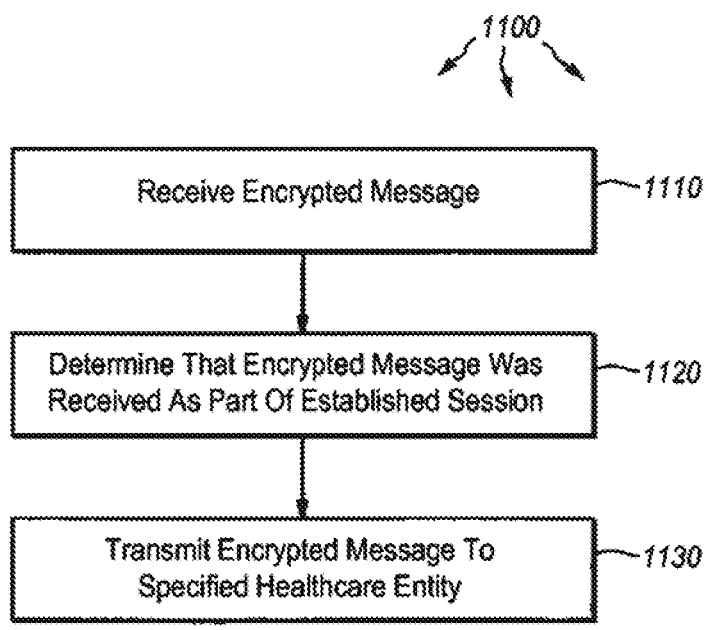
FIG. 11 illustrates a flowchart of an example method for providing a secure messaging service.

In view of the systems and architectures described above, methodologies that may be implemented in accordance with the disclosed subject matter will be better appreciated with reference to the flow charts of FIGS. 10 and 11. For purposes of simplicity of explanation, the methodologies are shown and described as a series of blocks. However, it should be understood and appreciated that the claimed subject matter is not limited by the order of the blocks, as some blocks may occur in different orders and/or concurrently with other blocks from what is depicted and described herein. Moreover, not all illustrated blocks may be required to implement the methodologies described hereinafter.

FIG. 10 illustrates a flowchart of a method 1000 for securely messaging a healthcare entity. The method 1000 will now be described with frequent reference to the components and data of environment 900.

Method 1000 includes receiving an input from a user indicating that a message including one or more characters is to be securely transmitted to a specified healthcare entity, the message being part of a conversation between a user and the specified healthcare entity (1010). The communications module 904 of the mobile device 901 may receive input 906 from user 905 indicating that a message including text or other characters is to be transmitted to a doctor, pharmacist, hospital or other healthcare entity 919. This message may be the first of a string of messages that are part of a conversation. The conversation may include the user and one or more healthcare entities, and may include messages sent between healthcare entities that are not sent to the user.

Method 1000 further includes encrypting the one or more characters of the message using at least one encryption algorithm, such that the message is encrypted during the transfer from the user to the specified healthcare entity (1020). The encryption module 907 may encrypt the inputted text characters using any one or more of a plurality of different encryption algorithms 908. The encryption module 907 may encrypt all or select portions of the message 915. In some cases, the encrypted message may include portions of metadata that are or are not encrypted that include data about the user 905 and/or about the user's location or current state. The metadata may further include information indicating whether the user has authenticated to the secure messaging service 917 of computer system 911, and/or whether a session 918 has been established. The session 918 may be established between the user 905 and the secure messaging service 917, and may be expandable to include other healthcare entities. Alternatively, each user and healthcare entity may establish their own separate session with the secure messaging service 917. These sessions may be established through the messenger application 910A/910B, through a web page or through some other means of authentication.

Method 1000 also includes an act of initiating transmission of the encrypted message such that the encrypted message is sent to the specified healthcare entity, wherein the encrypted message is transferred in accordance with legal regulations governing healthcare communications (1030). Thus, the messenger application 910A or the communications module 904 may initiate transmission of the encrypted message 915 to at least one healthcare entity 919. The encrypted message may be sent directly to a specified healthcare entity or may be routed through one or more intervening computer systems. For example, the encrypted message 915 may be sent to the secure messaging service 917 of computer system 911. Thus, the communications module 914 of computer system 911 may receive the encrypted message and may analyze any associated metadata to determine details about the sender (e.g. user 905).

Figure 15:
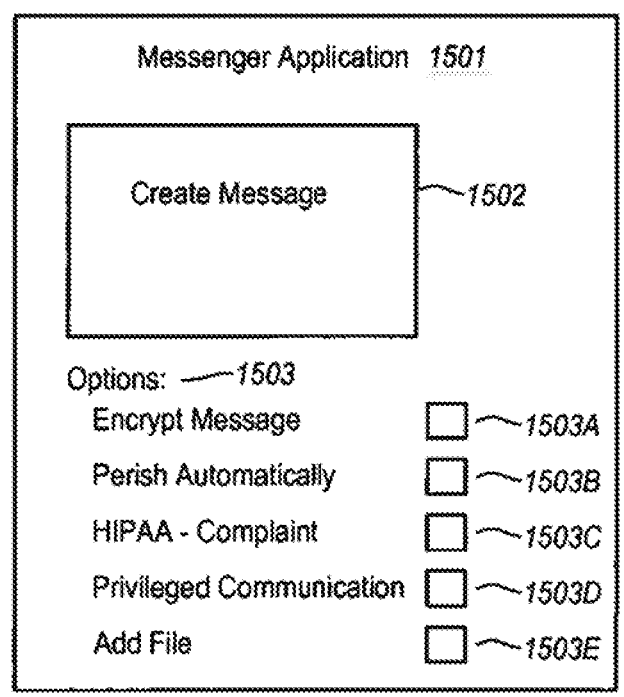
FIG. 15 illustrates an embodiment of a messenger application that provides various message-related options.

In some cases, for example, as shown in FIG. 15, a messenger application 1501 (which may be the same as or different than messenger application 910A) may provide various options 1503 to the user. The user may create a message by entering text in the window provided 1502. The user may then be able to select various options including whether to encrypt the message (1503A), whether to have the message (or conversation) perish automatically upon delivery or completion or upon determining that a certain time period has elapsed since the transfer of the message (1503B), whether the message is to be sent in a HIPAA-compliant manner (1503C), whether the message is a privileged communication (e.g. as between a lawyer and a client) (1503D), or whether the user would like to add a file to the message (1503E). Many other options may be provided that are not shown in FIG. 15.

Metadata sent along with the message may indicate whether any of these options have been selected. Some of the options may necessitate the selection of other options. For instance, selecting the HIPAA-compliant option 1503C may automatically select the encrypt message option 1503A). Similarly, selecting the privileged communication option 1503D may automatically select the perish automatically option 1503B. Some options, when selected, may cause processing to occur prior to transmission (e.g. encryption) while other options may cause processing to occur on intervening computer systems such as 911 or on other user's or healthcare entity's computing systems. Thus, in this manner, a user may select how the user wants their message to be sent, and what is to occur to their message after being sent (or after being read by the recipient). In some cases, these selected options may be overridden by other concerns such as regulations governing healthcare-related communications. For instance, if user 905 selects the HIPAA-compliant option 1503C and the perish automatically option 1503B, the perish automatically option will likely need to be ignored, as HIPAA compliance requires most types of healthcare-related communications to be stored, at least for some period of time. Thus, in such cases, option 1503C would trump option 1503B, and the messages would be stored and would not perish automatically. Policies may be established and promulgated by the secure messaging service 917 to determine which selectable options are ultimately applied to a given message.

In cases where messages or at least portions of message data is to be retained, that data may be retained on computer-readable storage media on the mobile device 901, on computer system 911 (or on a database accessible thereto), on a healthcare entity's computer system or on another system. When these messages are stored, they may be stored in accordance with legal guidelines regulating healthcare communications (e.g. HIPAA-specified regulations). In cases where the messages are to perish automatically after being read or after the conversation is finished, the storage on computer systems 901 or 911 may be configured not to store messages or conversation-related data such as metadata.

In cases where messages are to be stored (e.g. when HIPAA-compliant messages are sent between doctors and users), the messages may be store in encrypted form and may only be accessible to authenticated users that have the proper credentials (i.e. they have the proper keys to decrypt the messages). Because the stored messages are encrypted, intervening entities involved in transmission between the user and the healthcare entity are prevented from accessing the encrypted messages.

In some embodiments, user 905 may select which healthcare entity to send a message to by typing in the healthcare entity's name or by selecting a picture of the healthcare entity. For example, the messenger application 910A may display a picture of a doctor or a particular doctor's office. The user 905 may select that picture and begin typing their message. Once typed, the message is encrypted and transmitted to the specified healthcare entity in a HIPAA-compliant manner. In some cases, the messenger application 910A may determine, based on who the message is being sent to, that the message is to be sent in a HIPAA-compliant manner. In other cases, the user 905 may simply select HIPAA-compliance as an option for that message or conversation. The encrypted message 915 is then transmitted to the specified healthcare entity over one or more computer systems including computer system 911.

As mentioned above, the messenger application 910A may include an authentication module that is configured to authenticate the user prior to facilitating message transmission. Similarly, each healthcare entity's messenger application 910B may also be configured to receive authentication credentials from the healthcare entity and authenticate the entity before they can access received messages or send messages themselves. Once the user and the healthcare entity are authenticated to their own separate instances of the messenger application, the messages 915 are transmitted and received as push messages between the messenger application instances. In some embodiments, as will be shown further below, the messenger application 910A may provide portions of structural data that allow the healthcare entity to perform one or more specified functions such as filling prescriptions or filling out insurance or other forms.

FIG. 11 illustrates a flowchart of a method 1100 for providing a secure messaging service. The method 1100 will now be described with frequent reference to the components and data of environment 900 of FIG. 9.

Method 1100 includes receiving, at the secure messaging service, an encrypted message that includes message content intended for a specified healthcare entity, the encrypted message being part of a conversation between a user and the specified healthcare entity (1110). For example, secure messaging service 917 may receive encrypted message 915 that includes the content of the message as well as any corresponding metadata. The determining module 916 may be configured to determine that the encrypted message 915 was received as part of an established session 918 between the secure messaging service and a user-side instance of a messenger application (1120). The communications module 914 of computer system 911 may then transmit the encrypted message to the specified healthcare entity 919, the specified healthcare entity can access the encrypted message via an instance of the messenger application 910B (1130).

Figure 12:
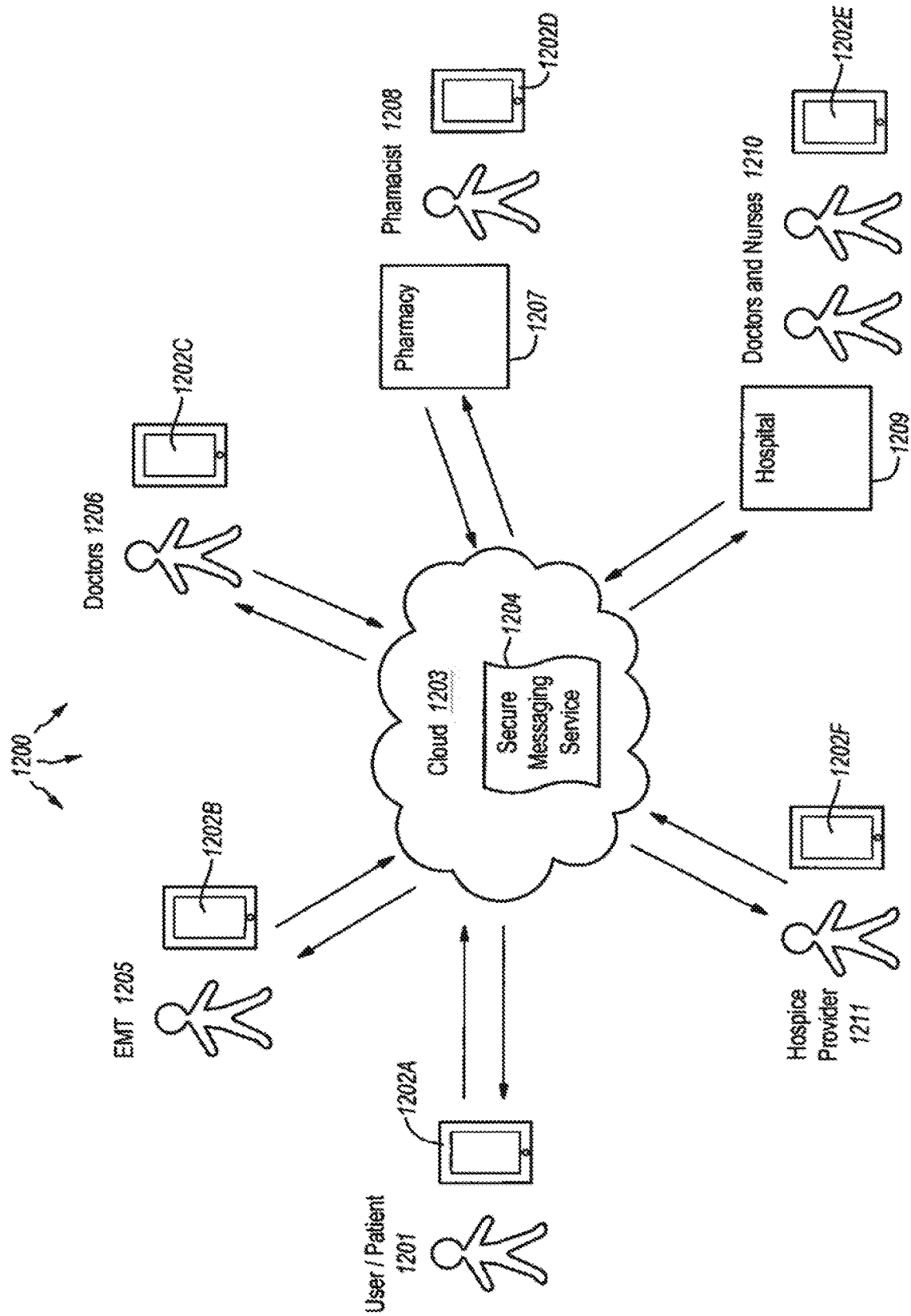
FIG. 12 illustrates a computing environment in which users and healthcare entities may send and receive secure messages to and from each other.

As shown in environment 1200 of FIG. 12, the user/patient 1201 may use a messenger application 1202A on their mobile or other device to the secure messaging service 1204 which is hosted on one or more virtual or physical computer system on the cloud 1203. The secure messaging service 1204 may store and/or pass the message on to one or more specified healthcare recipients. For example, the user 1201 may directly message their doctor 1206 to request a prescription, or may directly message a doctor's office to request an appointment, or may message a nurse or doctor 1210 at a hospital 1209 to inquire on the health status of a relative. In some cases, healthcare providers may message each other using the secure messaging service 1204. For instance, an emergency medical technician (EMT) 1205 may use their messenger application 1202B to message the hospital 1209 to notify them of a patient's current state, or a doctor 1206 may use their messenger application 1202C to message a pharmacy 1207 or pharmacist 1208 to call in a prescription for a patient, or the doctor 1206 may message a hospice provider 1211 with questions regarding a current or former patient. Each of these healthcare providers may use their messenger applications (e.g. 1202B, 1202C, 1202D, 1202E, 1202F) to reply back to any received messages. In this manner, healthcare providers and patients may communicate over secure channels in a HIPAA-compliant manner. It will be understood that the present application is not limited to those healthcare entities shown in FIG. 12, and that many other entities (including non-healthcare entities) may use the secure messaging service 1204 to send secure messages.

Figure 13:
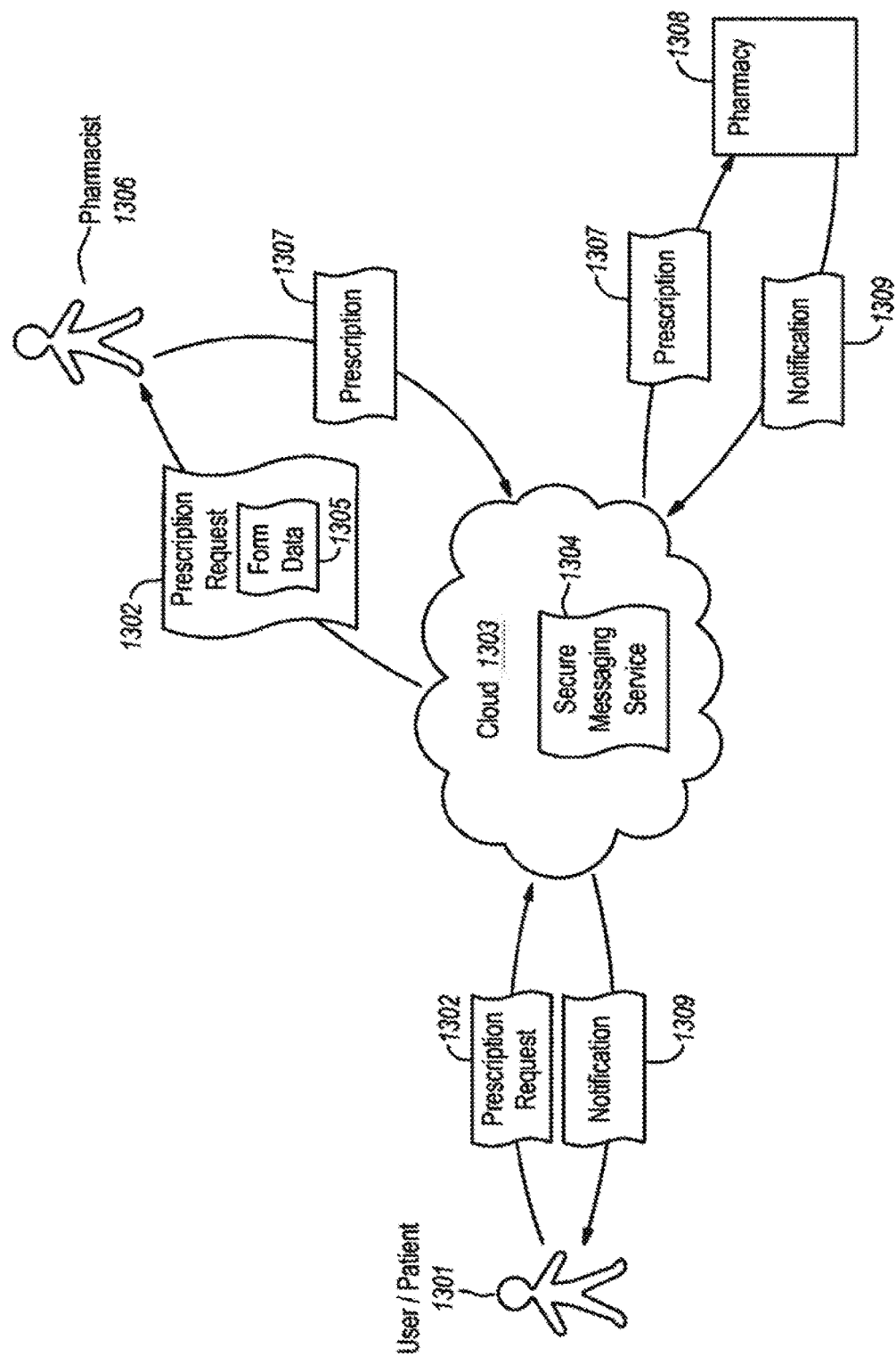
FIG. 13 illustrates a computing environment in which a user requests a prescription from a doctor and receives notification that the prescription has been filled by a pharmacy.

In one embodiment, as shown in FIG. 13, a user or patient 1301 may use secure messaging service 1304 to request that a prescription be filled or refilled. The user 1301 may initiate transmission of a prescription request 1302. That request is sent to the doctor 1306 (or pharmacist) through the secure messaging service 1304, which is hosted in the cloud 1303. The prescription request 1302 may include form data 1305 that allows the doctor to easily fill in data for the prescription. The form data may also include insurance and other appertaining information. The doctor 1306 may then send the prescription 1307 to a specified pharmacy 1308 via the secure messaging service 1304. Once the prescription 1307 has been filed, the pharmacy may use their messenger application to send a notification 1309 to the user/patient 1301 indicating that the prescription is ready for pickup. The doctor may message in the prescription to substantially any pharmacy, including one the user has previously used (perhaps many times) or to a new pharmacy (perhaps one that is currently located near the user (as determined by GPS on the user's mobile device)). In this manner, the secure messaging service 1304 can facilitate fulfillment of prescriptions for users.

Figure 14:
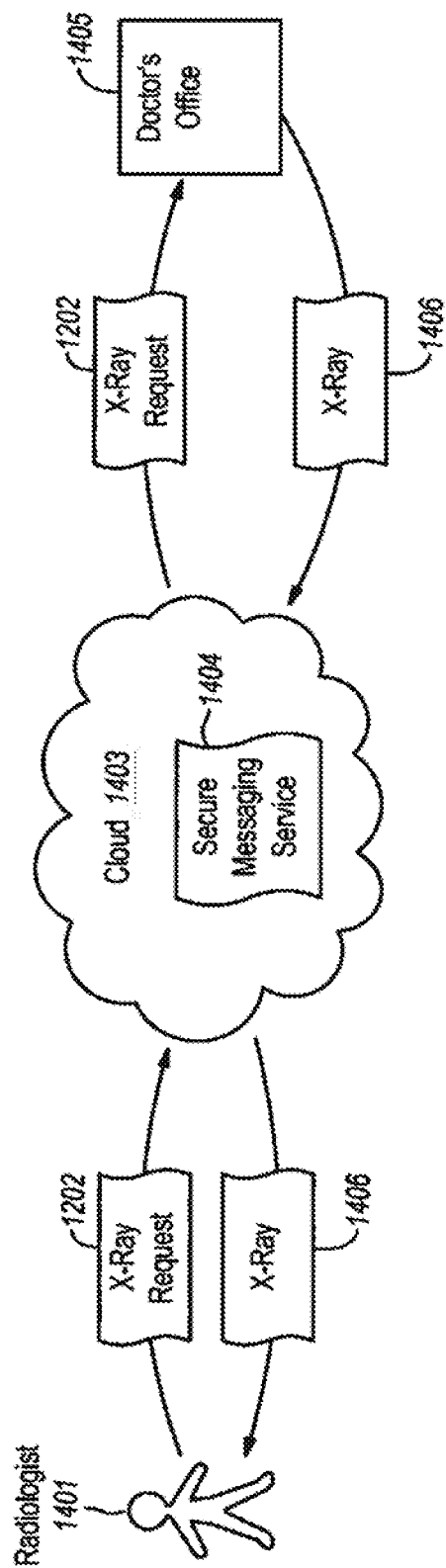
FIG. 14 illustrates a computing environment in which a doctor requests and receives an X-ray using the secure messaging service.

In another embodiment, as shown in FIG. 14, users of the secure messaging service 1404 may use the service to send files securely. For example, a radiologist 1401 may send a request for an X-ray 1202 to a doctor's office through the secure messaging service 1404. The secure messaging service 1404, hosted on cloud 1403, may send that X-ray request 1202 on to the doctor's office 1405, where the doctor's office is notified that the radiologist's request has been received. The doctor's office 1405 may then attach a file including the patient's X-rays 1406 and message it to the radiologist via the secure messaging service 1404. It will be understood that many other use scenarios are possible, and that these are just a few of many different examples of healthcare entities securely messaging each other in the course of their everyday duties.

When prescriptions are filled or when files are transferred, the secure messaging service 1204 of FIG. 12 may be configured to store the corresponding encrypted messages in a data store. The stored messages are thus auditable and retrievable for at least a specified amount of time. Regulations governing the transmission of healthcare communications (or potentially legal or other professional communications) may dictate how long the messages and/or corresponding metadata are stored. In cases where the message is sent to a lawyer and the message is intended to be privileged, the message may perish automatically upon being read by the receiving entity. In cases where the message is sent in a HIPAA-compliant manner, the message is encrypted and is only accessible by healthcare entities that are authorized to view the message or conversation. Each healthcare entity can use their own messenger application instance to authenticate to the secure messaging service and communicate with other healthcare entities and/or the patient using application push messages transferred in encrypted form over the internet.

Figure 16:
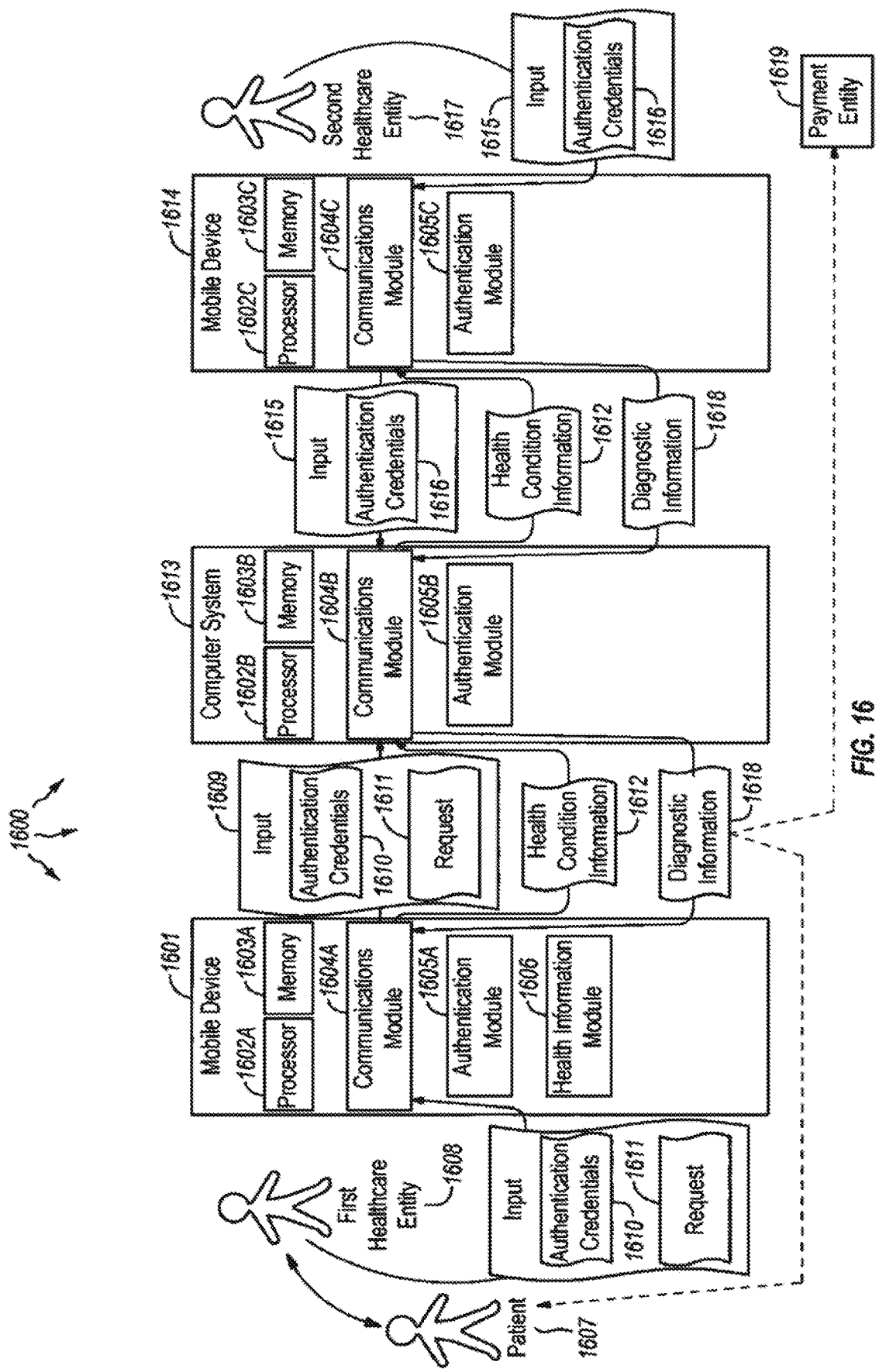
FIG. 16 illustrates a computing environment in which remote healthcare services are provided.

Turning now to FIG. 16, a computer architecture 1600 is illustrated in which at least one embodiment may be employed. Computer architecture 1600 includes multiple computer systems including mobile device 1601, computer system 1613 and mobile device 1614. Each computer system includes a processor (1602A, 1602B and 1602C, respectively), a memory (1603A, 1603B and 1603C, respectively), and a communications module (1604A, 1604B and 1604C, respectively). Although labeled "mobile device" or "computer system", it will be understood that each computing device may be any type of mobile or stationary, local or distributed computer system, including a cloud computing system. Each computer system includes modules for performing a variety of different functions.

For example, mobile device 1601 includes an authentication module 1605A. The authentication module 1605A may be configured to receive authentication credentials from one or more users and authenticate those users. In some embodiments, one form of authentication may take place on the mobile device 1601 (or 1614) while a second form of authentication may take place on computer system 1613. Thus, for instance, a user may login to a mobile device using a PIN number or other type of password or biometric authentication, and may login to the computer system 1613 (or to a service provided by the computer system 1613) using a different password or different type of authentication. Thus, at least in some embodiments, each computing device may have its own authentication module (i.e. 1605A, 1605B or 1605C, respectively).

The mobile device 1601 may also include a health information module 1606. The health information module 1606 may be configured to receive and/or store health information related to one or more patients. The health information may be entered directly into a health information application, or it may be received from one or more devices. For example, in cases where the first healthcare entity 1608 is a nurse working with patient 1607, the nurse may use a stethoscope or blood pressure cuff or other medical device to take health-related measurements for the patient. The nurse may then enter these measurements into a health information application, into a form or other information entry means. Additionally or alternatively, the medical device itself may be capable of providing health data directly to another computer system such as mobile device 1601 and/or computer system 1613. This information may be transferred and/or stored in a HIPAA-compliant manner. In some cases, this health information 1612 is transferred through computer system 1613 to mobile device 1614.

In cases where the second healthcare entity 1617 is a doctor of some type, the doctor may receive this health condition information 1612 and analyze it to determine a diagnosis for the patient 1607. The doctor may be remotely located from the patient, and may not be in the same state, country or continent. The doctor may view the measurement data taken by the nurse, and may also view live streaming information (e.g. from a probe or video camera) that may show the patient's inner ear, throat, or other bodily region of interest. The doctor may be able to determine that the patient has an ear infection, or has strep throat or has some other illness. It will be understood, of course, that these are very limited examples of remote diagnostics, and that substantially any type of medical device or data may provide data on substantially any type of disease or health condition that may be used by the doctor in his or her diagnosis.

Once the problem has been diagnosed, the doctor may send their diagnostic information 1618 either through computer system 1613 or directly to mobile device 1601. This diagnosis information may also be sent directly to the patient, and/or to a payment entity 1619. In some cases, the payment entity 1619 is a third party payment entity (e.g. a non-profit healthcare organization) that pays for medicines for patients who cannot afford them. Thus, the computer architecture 1600 of FIG. 16 allows health professionals to perform remote diagnostics and send those diagnostics to patients, healthcare providers such as nurses and/or to payment organizations. These concepts will be explained further below with regard to methods 1700 and 1800 of FIGS. 17 and 18, respectively.

Figure 17:
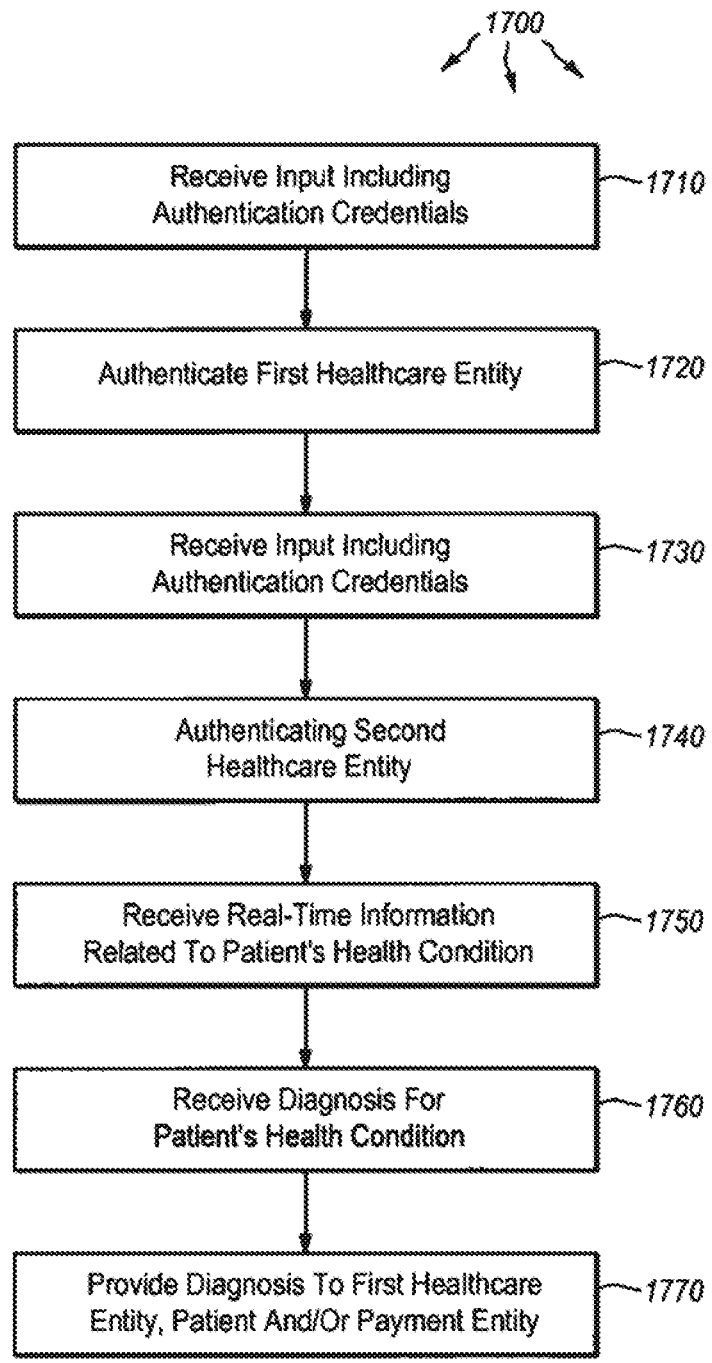
FIG. 17 illustrates an example flowchart of a method for providing remote healthcare services.
Figure 18:
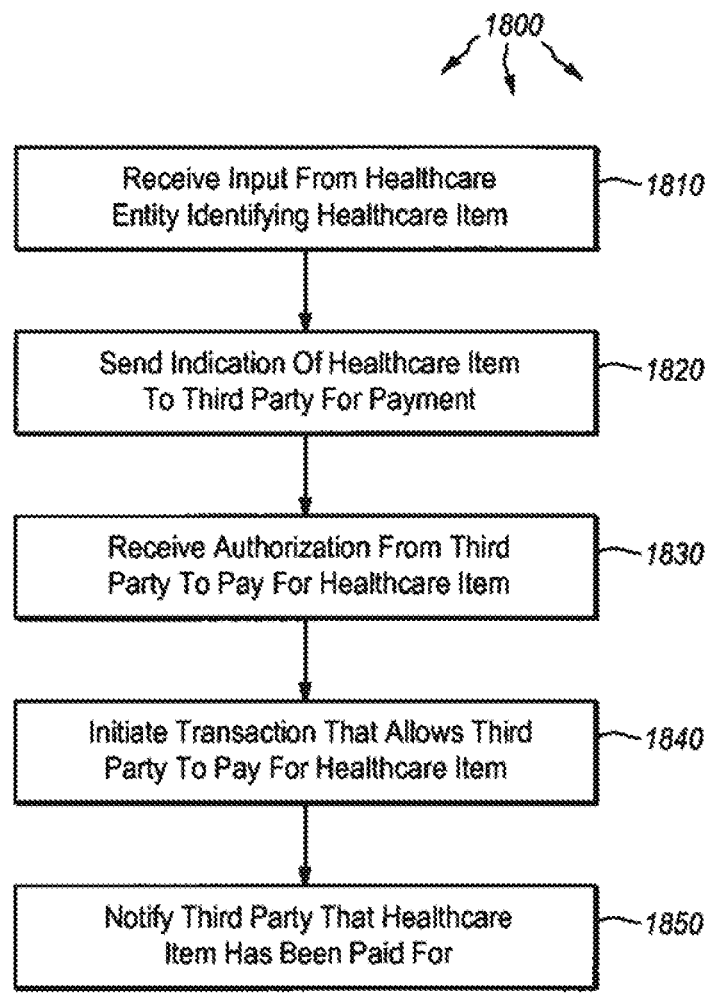
FIG. 18 illustrates an example flowchart of a method for facilitating a third-party healthcare payment.

In view of the systems and architectures described above, methodologies that may be implemented in accordance with the disclosed subject matter will be better appreciated with reference to the flow charts of FIGS. 17 and 18. For purposes of simplicity of explanation, the methodologies are shown and described as a series of blocks. However, it should be understood and appreciated that the claimed subject matter is not limited by the order of the blocks, as some blocks may occur in different orders and/or concurrently with other blocks from what is depicted and described herein. Moreover, not all illustrated blocks may be required to implement the methodologies described hereinafter.

FIG. 17 illustrates a flowchart of a method 1700 for providing remote healthcare services. The method 1700 will now be described with frequent reference to the components and data of environment 1600.

Method 1700 includes receiving an input from a first healthcare entity that includes one or more authentication credentials, the input requesting assistance from at least a second healthcare entity (1710). For example, computer system 1613 may receive input 1609 from first healthcare entity 1608. The input includes authentication credentials 1610 and a request for assistance 1611 from second healthcare entity 1617. The authentication credentials may include, for example, a username and password, a PIN number, biometric credentials such as a fingerprint or other types of credentials. Substantially any type of authentication algorithm or scheme may be used to authenticate the first healthcare entity 1608. As used herein, the terms "first healthcare entity" or "second healthcare entity" may refer to any of a variety of healthcare professionals (e.g. doctors, nurses, etc.), medical assistants, healthcare organizations, hospitals, doctors offices or other healthcare entities. In some embodiments, the first healthcare entity 1608 may be a nurse or medical assistant located in a place that is remote to the second healthcare entity 1617, which may be a doctor or other licensed medical professional. The healthcare entities may communicate with each other using the messenger application 910A/910B of FIG. 9, as will be explained further below.

Method 1700 includes authenticating the first healthcare entity using the authentication credentials received from the first healthcare entity (1720). Either the authentication module 1605A of mobile device 1601 or the authentication module 1605B or computer system 1613 may authenticate the first healthcare entity 1608 using authentication credentials 1610. Method 1700 also receives an input 1615 from the second healthcare entity 1617, where the input includes one or more authentication credentials 1616 identifying the second healthcare entity as one authorized to perform specified healthcare functions (1730). The credentials 1616 may authenticate a single user, such as a doctor, or may authenticate an organization or specified group of users. This group of users may collaborate on a given diagnosis to determine the best course of action for a given patient. In some embodiments, the doctors (i.e. second healthcare entity 1617) are volunteer doctors that donate their time to provide (remote) assistance to children and adults in other countries where a need for medical professionals exists.

Method 1700 further includes authenticating the second healthcare entity using the authentication credentials received from the second healthcare entity (1740). As above, either mobile device 1614 or computer system 1613 may authenticate the second healthcare entity 1617. The authentication may include identifying the second healthcare entity as a medical professional, assistant or entity that is authorized to provide a level of healthcare, including potentially diagnosing illnesses, treating diseases, prescribing medications, examining x-rays, analyzing blood results, or performing any of a wide variety of healthcare-related functions not mentioned. The second healthcare entity 1617 may receive (either directly or through computer system 1613) real-time information related to a health condition of at least one patient (1750). Thus, the second healthcare entity 1617 may receive health condition information 1612 from the first healthcare entity, which may be a nurse or assistant that is working with the patient 1706.

Method 1700 further includes receiving, from the second healthcare entity, one or more portions of diagnostic information related to the patient's health condition (1760) and providing the received diagnostic information to at least one of the following: the first healthcare entity, the patient and a payment entity (1770). In this manner, the second healthcare entity 1617 can view the totality of the health condition information 1612 including verbal descriptions from a nurse, test results, still images, live video feeds, instrumentation data from diagnostic devices or other health condition information, and make a determination as to the best course of action related to the patient 1607. The second healthcare entity (or group of entities such as collaborating doctors) may provide a diagnosis 1618 which is sent to the patient, to the first healthcare entity 1608 and/or to a payment entity 1619. In some embodiments, as will be described further below with regard to method 1800 of FIG. 18, the diagnosis may include a drug prescription or other prescribed course of action (e.g. a cast for a broken arm or a leg brace for a sprained knee). This prescribed drug or other course of action may be paid for or reimbursed by a payment entity 1619 such as a third-party non-profit organization.

In some embodiments, providing real-time health condition information 1612 to the second healthcare entity 1617 includes streaming images or video from the first healthcare entity 1608 to the second healthcare entity 1617. The video may include video taken from a mobile device's camera, video taken from a medical instrument such as a probe, still images taken with a digital camera or with the mobile device's camera, audio information such as verbal descriptions of the patient's medical issues or other health condition information.

Figure 20:
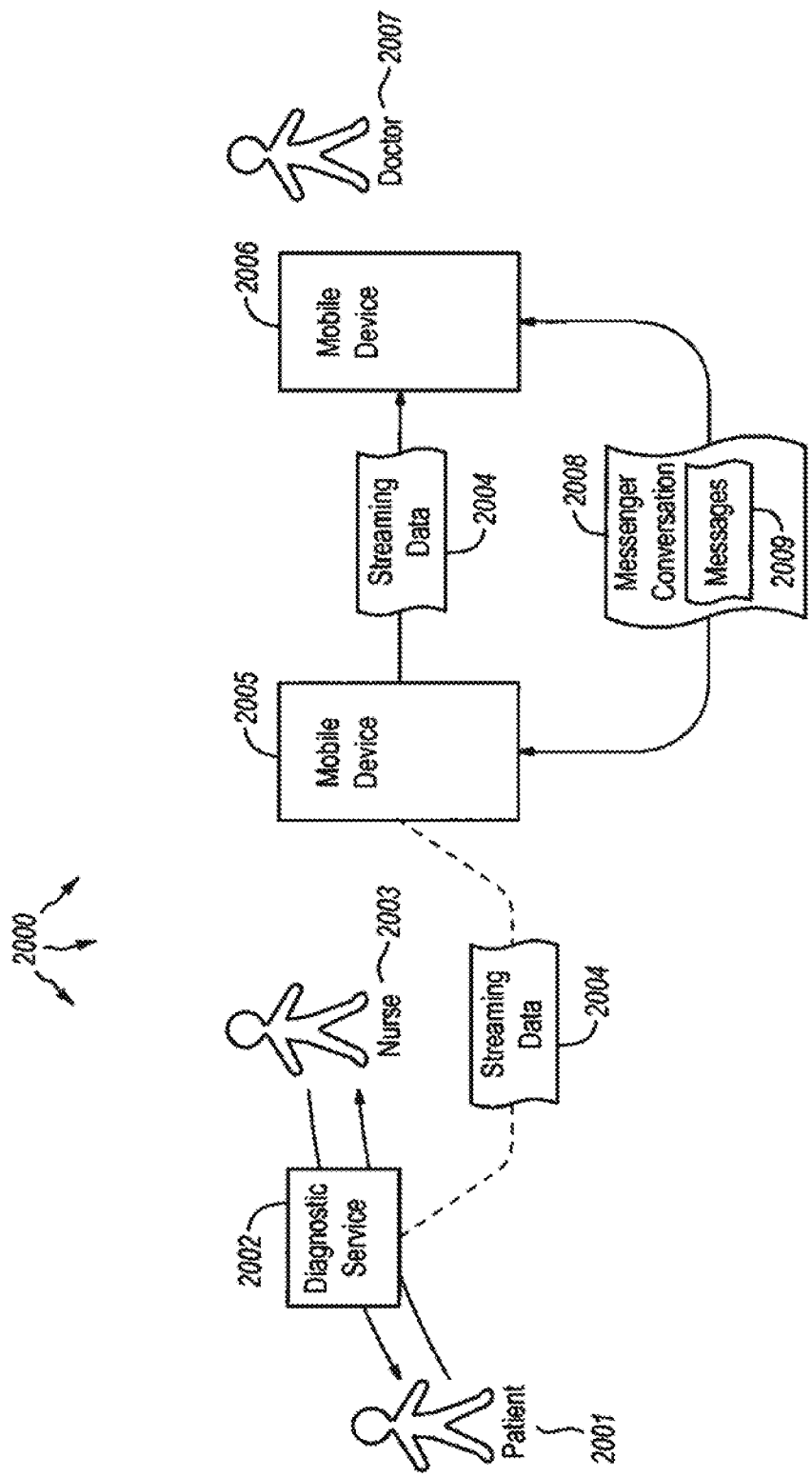
FIG. 20 illustrates a computing environment in which remote diagnostic services are provided.

As shown in environment 2000 of FIG. 20, a doctor 2007 or other health professional may use the real-time streaming data 2004 to assist in making a diagnosis. The real-time health condition streaming data may also be communicated to other entities using various forms of communication including a messenger application (e.g. 910A). The doctor 2007 and the nurse 2003 may each have mobile devices (2006 and 2005, respectively) which may be smartphones, tablets, laptops or other computing systems. The nurse 2003 may use the mobile device to take pictures, provide streaming video or perform other functions. In some cases, the nurse's mobile device 2005 may be used in combination with a diagnostic device 2002 (such as a stethoscope or an otoscope) to provide the streaming health condition data 2004. In other cases, the diagnostic device itself 2002 may have a communication means that allows it to transmit the streaming data 2004 to other entities. The nurse 2003 may thus analyze the patient's condition or provide health condition data for the patient 2001 to the doctor 2007.

In some cases, the nurse 2003 and doctor 2007 may use the secure messaging service 917 to conduct a real-time conversation 2008 over messenger application push messages 2009. In this manner, doctors and nurses (or other professionals) can communicate using text messages over a secure network (other than the traditional SMS text network). The text messages may be transmitted in a HIPAA-compliant manner, or may be transmitted in another manner that complies with regulations governing health-related communications in a foreign country. In cases where health condition information 1612 is transferred using messenger application messages, as shown in FIG. 16, diagnostic information 1618 may also be transferred between the first healthcare entity and the second healthcare entity using the messenger application. In this manner, information relating to the patient's health conditions and the patient's diagnosis may be transferred using the messenger application 910A/910B.

In cases where a third party payment entity 1619 pays for the patient's prescription or other prescribed course of action, the computer system 1613 may receive an indication from the third-party payment entity indicating that the medication or other specified course of action has been paid for. The computer system 1613 may then provide an indication to the first healthcare entity 1608 indicating that the specified medication has been paid for. Once the first healthcare entity receives this notification, they can give the patient the prescription, or in cases where the first healthcare entity is a pharmacy, the pharmacy can fill the prescription for the patient. The second healthcare entity 1617 may then be notified that the patient received the medication. Thus, a doctor may be able to view a patient's current condition, recommend a course of action, have that course of action paid for by a third party organization, and receive an indication that the intended course of action has been carried out (e.g. that the patient has received Amoxicillin for an ear infection).

Subsequently, the doctor or other healthcare entity (e.g. a doctor's office) may maintain contact with the patient using the messenger application. Such a messenger application allows the second healthcare entity to follow-up on the patient's prescription compliance to ensure that they are taking the prescribed medication or are wearing their brace or are otherwise complying with the doctor's wishes. Any or all of the health condition information 1612, the diagnostic information 1618, the payment information, the messenger application messages or other remote diagnostic-related information may be stored in a HIPAA-compliant manner, so as to ensure that the process is transacted within the confines of regulations governing the practice of medicine and the communication of patient health-related data.

FIG. 18 illustrates a flowchart of a method 1800 for facilitating a third-party healthcare payment. The method 1800 will now be described with frequent reference to the components and data of environment 1900 of FIG. 19.

Figure 19:
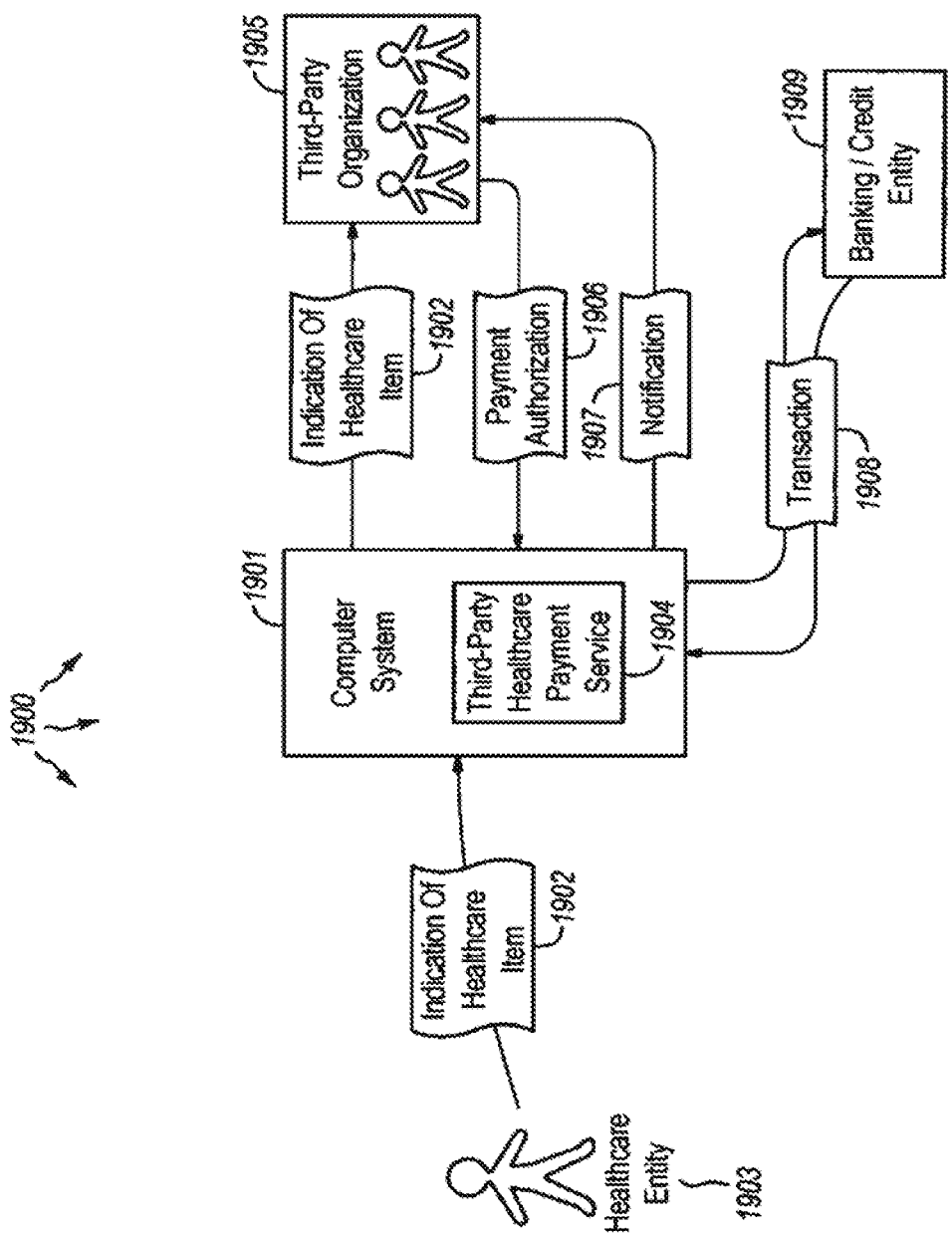
FIG. 19 illustrates a computing environment in which third-party healthcare payments are processed.

Method 1800 includes receiving an input from a healthcare entity identifying at least one healthcare item that is to be paid for by a third party, the healthcare entity being authenticated to a third-party healthcare payment service (1810). For example, as shown in FIG. 19, computer system 1901 may receive indication 1902 indicating one or more healthcare items. The indication 1902 may be sent by healthcare entity 1903. In some cases, the healthcare entity 1903 may be a doctor, nurse or other health professional.

Method 1800 next includes sending an indication of the at least one identified healthcare item to the third party for payment (1820). The computer system 1901 may thus send the healthcare item indication 1902 to a payment organization such as a third-party non-profit organization 1905 that has been established to pay for healthcare items. In some cases, the third-party organization 1905 may be designed to pay for prescriptions, vaccinations, casts, braces or any of a variety of other medical devices, tools, medicines or other related items which may be used to help a person heal from a malady of some sort. The third-party organization 1905 may pay for such items for persons who cannot afford those items themselves. Thus, for example, a nurse may examine a patient in a foreign country, have a doctor review the analysis or provide their own diagnosis, and have that doctor (e.g. 1903) indicate to a third-party organization that the patient's prescribed medical items are to be paid for.

Method 1800 further includes receiving authorization from the third party to pay for the at least one identified healthcare item (1830). Thus, computer system 1901 may receive a payment authorization 1906 from the third-party organization 1905. The payment authorization 1906 indicates that the third-party organization 1905 is willing to pay for the item(s) mentioned in the indication 1902. The third-party healthcare payment service 1904 of computer system 1901 may then initiate a transaction that allows the third party organization 1905 to pay for the identified healthcare item(s) (1840). The transaction 1908 may take place between a banking or credit entity 1909 and the third-party organization 1905. The third-party healthcare payment service may be configured to transfer money between the banking or credit entity 1909 and the third-party organization 1905. Once the transaction 1908 has completed, a notification 1907 is sent to the third party organization 1905 notifying them that the transaction is complete and that the identified healthcare item(s) has/have been paid for (1850).

In some embodiments, the third-party healthcare payment service may further notify at least one beneficiary that one or more of the identified healthcare item have been paid for by the third party. The third-party healthcare payment service may work in conjunction with the secure messaging service 917 of FIG. 9 to notify the third party organization 1905 that the transaction is complete and that the at least one identified healthcare item has been paid for. In this manner, the third-party healthcare payment service 19904 facilitates payments between third parties and banking or credit institutions. It will be understood that the third-party organization 1905 may be a single individual, a group of individuals or an entity (such as a non-profit entity or other organization). In some cases, members of the third-party organization 1905 may analyze and approve a diagnosis as being proper before a payment authorization is given. Such secondary analysis may be used to reduce fraud, ensuring that healthcare items are only purchased for those who are truly sick and need the items.

In another embodiment, a computer program product may be provided for implementing a method for providing a remote diagnostic for a patient. The computer program product includes one or more computer-readable storage media having stored thereon computer-executable instructions that, when executed by one or more processors of a computing system, cause the computing system to perform the method. The method may be from the perspective of the second healthcare entity 1617 of FIG. 16 (or from the perspective of their mobile device 1614). The method includes receiving an input 1615 from a user that includes one or more authentication credentials 1616 corresponding to the user 1617. The communications module 1604C of the mobile device 1614 may transmit the received authentication credentials 1616 to a remote diagnostic service. The mobile device 1614 may receive real-time information related to a health condition of at least one remotely-located patient, and may provide one or more portions of diagnostic information related to the patient's health condition to the remote diagnostic service for distribution to other healthcare entities (e.g. 1608), to the remotely-located patient 1607 or to a payment entity 1619.

Thus, as described above, a healthcare entity may work with a patient to determine the patient's current health condition. Information related to the patient's health can be sent to a remote doctor or other health professional. This doctor may reach a conclusion and provide a diagnosis that includes recommended healthcare items, such as prescriptions. This information may be sent to a third-party payment organization for payment, upon which the original healthcare entity is notified that the healthcare items were paid for and can now be distributed to the patient. The healthcare entities may communicate throughout the process using a secure messaging service and messenger applications which allow users and healthcare entities to communicate via text (or picture or video) messages in a secure and HIPAA-compliant manner. Other embodiments include a multi-access (HIPAA-compliant) health care provider portal which allows multiple different authenticated providers to access patients' medical records. Moreover, the portal allows specified portions of the medical records to be transmitted to certain care givers based on user-established policies. The portal further facilitates communication between care givers, including communication of a patient's prescription compliance data, and allows manufacturers and service providers to provide targeted items to users based on their health concerns.

The concepts and features described herein may be embodied in other specific forms without departing from their spirit or descriptive characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

The invention claimed is:

1. At a computer system including at least a processor and a memory, a computer-implemented method for providing remote healthcare services, the method comprising:
   in response to receiving a request for assistance from a first computing system, the first computing system associated with a first healthcare entity, transmitting, via one or more communication channels provided by a computerized integration tier, one or more portions of received real-time information related to at least one health condition of at least one user to a second computing system, the second computing system associated with a second healthcare entity, the integration tier being configured to manage communication sessions between participants, the integration tier including a communication application programming interface (API) and at least one other communication mechanism to accept messages from multiple different communication channels;
   receiving, from the second computing system, a message including one or more portions of diagnostic information related to the at least one user's health condition that the second healthcare entity has generated based on the received real-time health condition information;
   determining a current location of the at least one user using at least one global positioning system (GPS) radio configured to send and receive location-identifying signals;
   determining, based on the current location of the at least one user, that the message is to be electronically encrypted, the determination based, at least in part, on the at least one user being located in a specified location within which encryption is to be used;
   upon determining that the message is to be encrypted, providing a variable portion of encrypted received diagnostic information to the first computing system and a variable portion of the encrypted received diagnostic information to a payment entity according to an identity-based information dissemination policy governing how much health information each entity is permitted to access, wherein the diagnostic information provided to the payment entity includes an indication received, via the second computing system, from the second healthcare entity that a cost for prescribed healthcare treatment based on the diagnostic information is to be paid in real-time by the payment entity, wherein the integration tier in the computer system facilitates payment by the payment entity, the integration tier being configured to manage financial transaction sessions between participants of a transaction including the first healthcare entity, the second healthcare entity, the payment entity, and the at least one user;

analyzing the diagnostic information, prior to its transmission to the payment entity, to evaluate one or more elements of a diagnosis and ensure that the diagnosis is proper for the at least one health condition indicated in the diagnostic information in order to prevent payment for improper or unnecessary diagnoses; and upon receiving the indication that the prescribed healthcare treatment has been paid for by the payment entity, directing, via the first computing system, the first healthcare entity to carry out the prescribed healthcare treatment while the prescribed healthcare treatment is monitored by the second healthcare entity to ensure proper implementation.

2. The method of claim 1, wherein providing the at least one real-time health condition information to the second computing system comprises streaming images or video from the first healthcare entity to the second healthcare entity.

3. The method of claim 2, further comprising:
receiving a first input from the first computing system that includes one or more first authentication credentials, the first input requesting assistance from at least the second computing system;
authenticating the first healthcare entity using the one or more first authentication credentials received from the first computing system;
receiving a second input from the second computing system, the second input including one or more second authentication credentials identifying the second healthcare entity as one authorized to perform specified healthcare functions; and
authenticating the second healthcare entity using the one or more second authentication credentials received from the second computing system.

4. The method of claim 1, wherein one or more messages are transferred between the first computing system and the second computing system using a messenger application.

5. The method of claim 4, wherein the one or more messages are transmitted in a manner that is compliant with one or more health regulations governing the transfer or storage of medical records.

6. The method of claim 4, wherein the diagnostic information is included in at least one of the one or more messages transferred between the first computing system and the second computing system using the messenger application.

7. The method of claim 1, wherein the payment entity comprises a third-party payment entity.

8. The method of claim 7, further comprising:
receiving the indication from the third-party payment entity that at least one specified medication has been paid for; and
providing the indication to the first computing system indicating that the at least one specified medication has been paid for, such that the first healthcare entity provides the at least one specified medication to the at least one user.

9. The method of claim 8, wherein the second healthcare entity is notified, via the second computing system, that the at least one user received the at least one specified medication.

10. The method of claim 9, wherein the second healthcare entity maintains contact with the at least one user using a messenger application.

11. The method of claim 10, wherein the messenger application allows the second healthcare entity to follow-up on the at least one user's prescription compliance.

12. The method of claim 1, wherein determining that the first healthcare entity or the second healthcare entity is in the specified location is performed by querying the GPS radio.

13. A computer system comprising the following:
one or more processors;
system memory;
at least one computer-readable hardware storage device having stored thereon computer-executable instructions that, when executed by the one or more processors, cause the computer system to:
in response to receiving a request for assistance from a first computing system, the first computing system associated with a first healthcare entity, transmit, via one or more communication channels provided by a computerized integration tier, one or more portions of received real-time health condition information related to at least one health condition of patient to a second computing system, the second computing system associated with a second healthcare entity, the integration tier being configured to manage communication sessions between participants, the integration tier including a communication application programming interface (API) and at least one other communication mechanism to accept messages from multiple different communication channels;
receive, from the second computing system, a message including one or more portions of diagnostic information related to the patient's at least one health condition that the second healthcare entity has generated based on the one or more portions of the received real-time health condition information;
determine a current location of the patient using at least one radio configured to send and receive location-identifying signals;
determine, based on the current location of the patient; that the message is to be electronically encrypted, the determination based, at least in part, on the patient being located in a specified location within which encryption is to be used;
upon determining that the message is to be encrypted, provide a variable portion of encrypted received diagnostic information to the first healthcare entity and a variable portion of the encrypted received diagnostic information to a payment entity according to an identity-based information dissemination policy governing how much health information each entity is permitted to access, wherein the variable portion of encrypted received diagnostic information provided to the payment entity includes an indication from the second healthcare entity that a cost for prescribed healthcare treatment based on the diagnostic information is to be paid in real-time by the payment entity, wherein the integration tier in the computer system facilitates payment by the payment entity, the integration tier being configured to manage financial transaction sessions between participants of a transaction including the first healthcare entity, the second healthcare entity, the payment entity, and the patient;
analyze the diagnostic information, prior to its transmission to the payment entity, to evaluate one or more elements of a diagnosis and ensure that the diagnosis is proper for the at least one health condition indicated in the diagnostic information in order to prevent payment for improper or unnecessary diagnoses; and upon receiving the indication that the prescribed healthcare treatment has been paid for by the payment entity, directing the first healthcare entity to carry out the prescribed healthcare treatment while the prescribed healthcare treatment is monitored by the second healthcare entity to ensure proper implementation.

14. The computer system of claim 13, wherein a messenger application communicates the diagnostic information from the second healthcare entity to the first healthcare entity, the diagnostic information being communicated in a manner that is compliant with one or more health regulations governing the transfer or storage of medical records.

15. The computer system of claim 13, wherein the payment entity comprises a third-party payment entity.

16. The computer system of claim 15, wherein the computer-executable instructions further configure the computer system to:
  receive the indication from the third-party payment entity that at least one specified medication has been paid for; and
  provide the indication to the first healthcare entity indicating that the at least one specified medication has been paid for, such that the first healthcare entity provides the at least one specified medication to the patient.

17. A computer program product for implementing a method for providing a remote diagnostic for patient, the computer program product comprising at least one computer-readable hardware storage device having stored thereon computer-executable instructions that, when executed by one or more processors of a computing system, cause the computing system to perform a method, the method comprising:
  receiving a first input from a first computing system, the first computing system associated with a first healthcare entity, the first input including one or more first authentication credentials, the first input requesting assistance from at least a second healthcare entity;
  authenticating the first healthcare entity using the one or more first authentication credentials received from the first computing system;
  receiving a second input from a second computing system, the second computing system associated with the second healthcare entity, the second input including one or more second authentication credentials identifying the second healthcare entity as one authorized to perform specified healthcare functions;
  authenticating the second healthcare entity using the one or more second authentication credentials received from the second computing system;
  in response to receiving a request for assistance from the first healthcare entity, transmitting, via one or more communication channels provided by a computerized integration tier, one or more portions of received real-time health condition information related to at least one health condition of patient to the second healthcare entity, the integration tier being configured to manage communication sessions between participants, the integration tier including a communication application programming interface (API) and at least one other communication mechanism to accept messages from multiple different communication channels;
  receiving, from the second computing system, a message including one or more portions of diagnostic information related to the patient's at least one health condition that the second healthcare entity has generated based on the received real-time health condition information;
  determining a GPS-provided current location of the patient using at least one GPS radio configured to send and receive location-identifying signals;
  determining, based, at least in part, on the UPS-provided current location of the patient, that the message is to be encrypted, the determination based at least in part on the patient being located in a specified location within which encryption is to be used;
  electronically encrypting the message; and
  providing a variable portion of encrypted received diagnostic information to the first computing system and a variable portion of the encrypted received diagnostic information to a payment entity according to an identity-based information dissemination policy governing how much health information each entity is permitted to access, wherein:
    the variable portion of encrypted received diagnostic information diagnostic information provided to the payment entity includes an indication from the second healthcare entity that a cost for prescribed healthcare treatment based on the diagnostic information is to be paid in real-time by the payment entity;
    the integration tier in the computer system facilitates payment by the payment entity, the integration tier being configured to manage financial transaction sessions between participants of a transaction including the first healthcare entity, the second healthcare entity, the payment entity, and the patient; analyzing the diagnostic information, prior to its transmission to the payment entity, to evaluate one or more elements of a diagnosis and ensure that the diagnosis is proper for the at least one health condition indicated in the diagnostic information in order to prevent payment for improper or unnecessary diagnoses; and
    upon receiving the indication that the prescribed healthcare treatment has been paid for by the payment entity, directing the first healthcare entity to carry out the prescribed healthcare treatment while the healthcare treatment is monitored by the second healthcare entity to ensure proper implementation.

* * * * *